United States Patent

Tajima

(10) Patent No.: US 9,232,620 B2
(45) Date of Patent: Jan. 5, 2016

(54) RADIOGRAPHIC IMAGING DEVICE AND METHOD WITH STOP TIMING BASED ON DOSAGE DETECTION

(71) Applicant: FUJIFILM Corporation, Tokyo (JP)

(72) Inventor: Takashi Tajima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 483 days.

(21) Appl. No.: 13/692,542

(22) Filed: Dec. 3, 2012

(65) Prior Publication Data

US 2013/0148784 A1 Jun. 13, 2013

(30) Foreign Application Priority Data

Dec. 8, 2011 (JP) .................................. 2011-269123
Sep. 13, 2012 (JP) .................................. 2012-201555

(51) Int. Cl.
*H05G 1/42* (2006.01)
*G01N 23/04* (2006.01)
*A61B 6/00* (2006.01)

(52) U.S. Cl.
CPC ............... *H05G 1/42* (2013.01); *A61B 6/4283* (2013.01); *A61B 6/542* (2013.01); *A61B 6/56* (2013.01); *G01N 23/04* (2013.01)

(58) Field of Classification Search
CPC ............. H05G 1/40; H05G 1/42; H05G 1/44; H05G 1/30; A61B 6/542
See application file for complete search history.

(56) References Cited

U.S. PATENT DOCUMENTS

| | | | | |
|---|---|---|---|---|
| 6,094,473 A | * | 7/2000 | Yu | H05G 1/38 378/108 |
| 6,138,019 A | * | 10/2000 | Trompower et al. | 455/436 |
| 6,445,930 B1 | * | 9/2002 | Bartelme et al. | 455/522 |
| 6,507,639 B1 | | 1/2003 | Popescu | |
| 2003/0012340 A1 | * | 1/2003 | Chornenky | 378/122 |
| 2005/0078792 A1 | * | 4/2005 | Strommer | 378/96 |
| 2005/0184773 A1 | * | 8/2005 | Boyko et al. | 327/156 |
| 2006/0023839 A1 | * | 2/2006 | Shoji | 378/97 |
| 2007/0274449 A1 | * | 11/2007 | Camus et al. | 378/98.12 |
| 2008/0114427 A1 | * | 5/2008 | Korb et al. | 607/96 |
| 2008/0317205 A1 | * | 12/2008 | Inuga et al. | 378/97 |
| 2009/0087073 A1 | * | 4/2009 | Kito et al. | 382/132 |
| 2012/0027180 A1 | * | 2/2012 | Tsuchiya | A61B 6/4233 378/114 |
| 2012/0297405 A1 | * | 11/2012 | Zhang et al. | 725/9 |

FOREIGN PATENT DOCUMENTS

JP 2008-86358 A 4/2008

\* cited by examiner

*Primary Examiner* — Brooke Purinton
(74) *Attorney, Agent, or Firm* — Birch, Stewart, Kolasch & Birch, LLP

(57) ABSTRACT

An AEC unit of an electronic cassette sets a dose target value and a short-circuited pixel used for AEC based on a radiographing condition. When a control unit of the electronic cassette detects start of irradiation of X rays, the AEC unit starts integration of a cumulative dose of X rays which are incident to a target region based on a dose detection signal output by the short-circuited pixel. The AEC unit predicts a stop timing at the time point t1, waits until the time point t2 which is a predetermined time earlier than a scheduled stop time, and sends a stop timing notification to an X-ray generation device at the time point t2. When the stop timing notification is received, a X-ray source control device immediately inputs an irradiation stop command so as to stop an operation of an X-ray source.

25 Claims, 39 Drawing Sheets

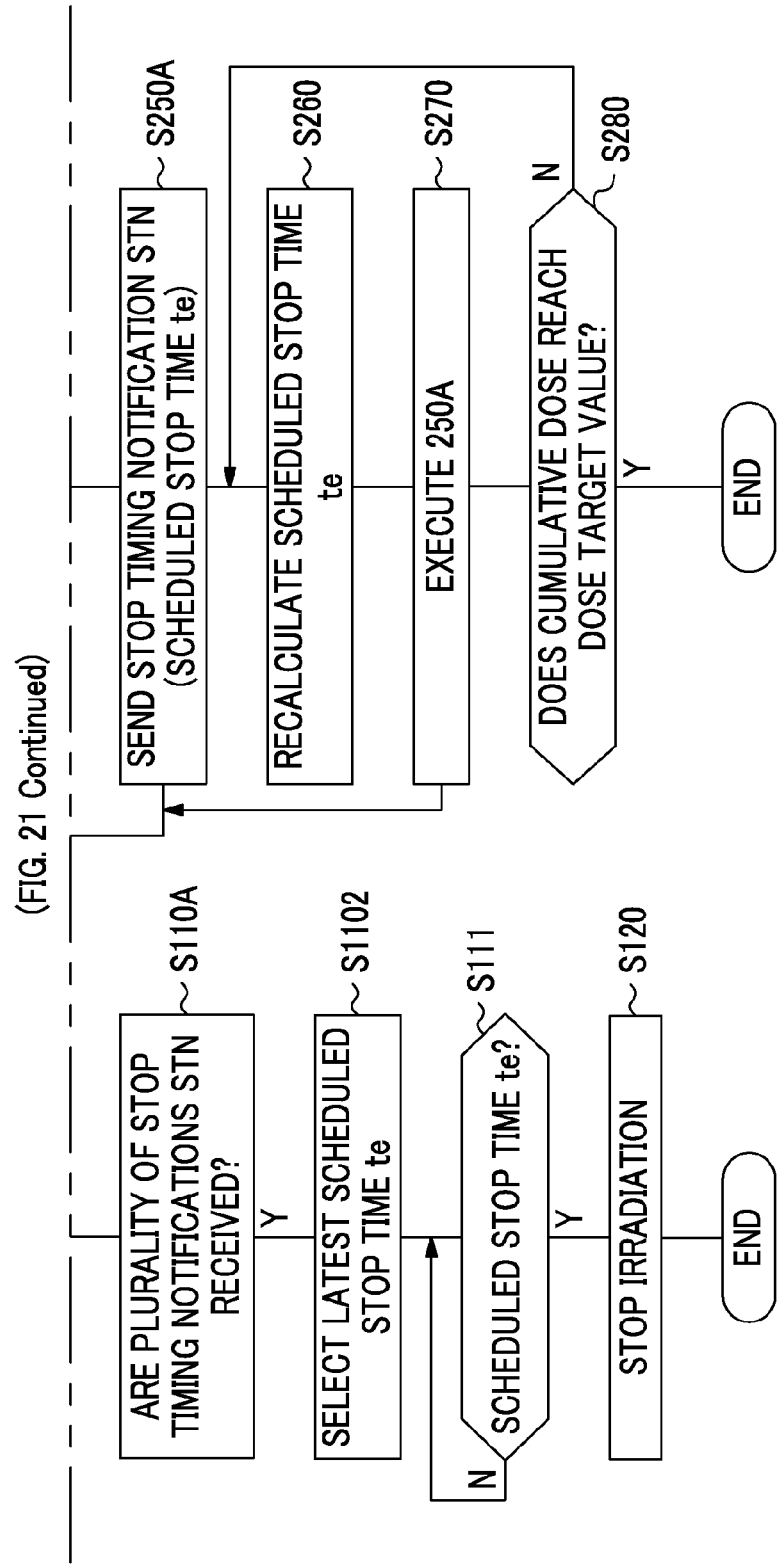

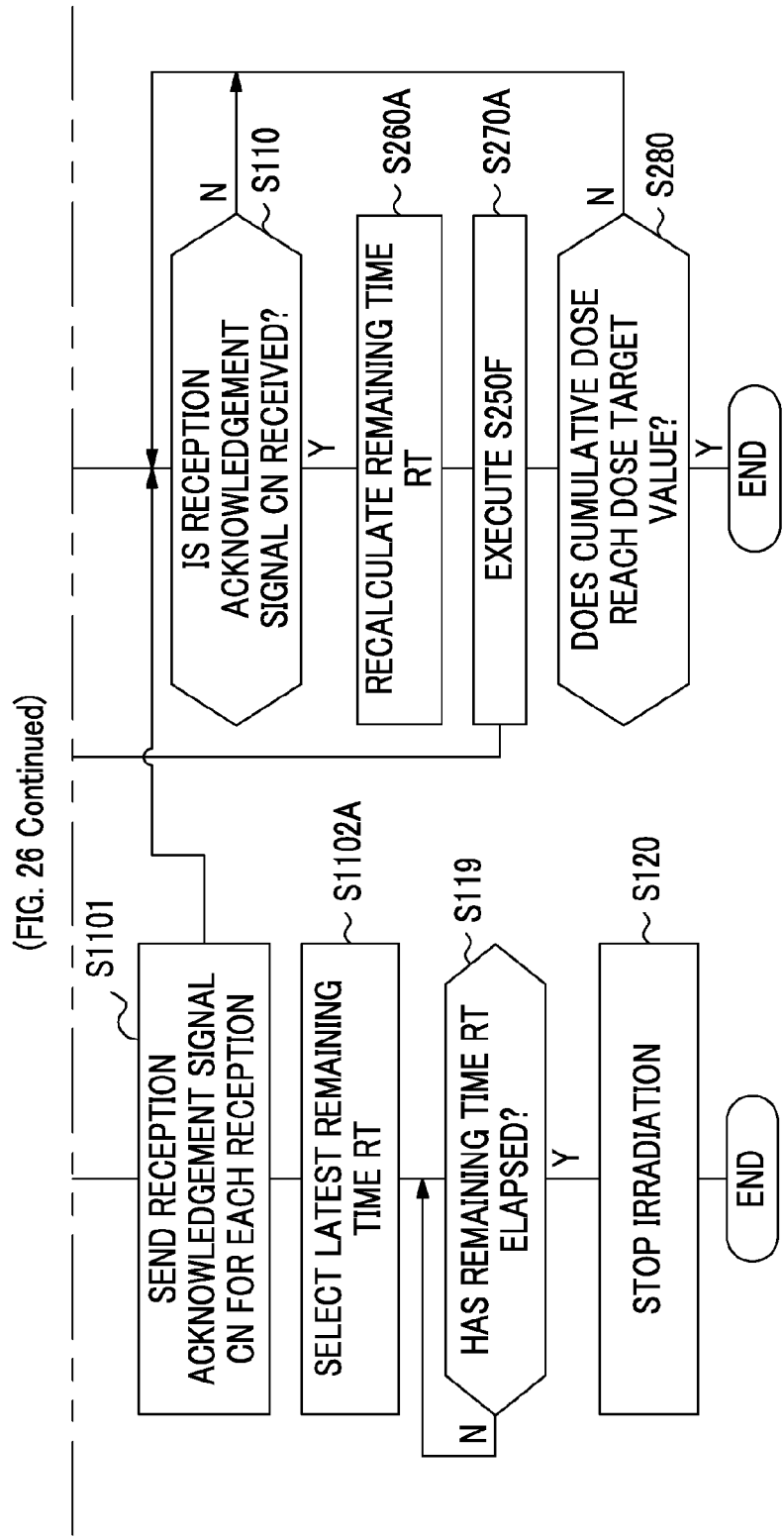
(FIG. 26 Continued)

RADIOGRAPHIC IMAGING DEVICE AND METHOD WITH STOP TIMING BASED ON DOSAGE DETECTION

BACKGROUND OF THE INVENTION

1. Field of the Invention

The present invention relates to a radiographic device which radiographs a radiological image from radiation transferred through a subject, a radiographic system using the radiographic device, and a control method and a recording medium for the radiographic device.

2. Description of the Related Art

In a medical field, an X-ray radiographing system using radiation, for example, X rays, is known. The X-ray radiographing system includes an X-ray generation device which has an X-ray source generating X rays, and an X-ray radiographing device which receives irradiation of X rays generated by the X-ray source and transferred through a subject and radiographs an X-ray image indicating image information of the subject.

The X-ray radiographing device includes an X-ray image detection device and a console. An X-ray image detection device which uses a flat panel detector (FPD) instead of an X-ray film or an imaging plate (IP) in the related art is put into practical use. The FPD is one in which pixels accumulating signal charges corresponding to a dose of X rays which are incident are arranged in a matrix, and converts the signal charge accumulated in each pixel into a voltage signal using a signal processing circuit so as to detect an X-ray image indicating image information of a subject, and outputs the X-ray image as digital image data. The console performs various settings for the X-ray image detection device, and performs image processes on the image data output by the X-ray image detection device.

As disclosed in JP2008-086358A, in an X-ray radiographing system, in order to suppress an exposure dose of a subject and obtain an X-ray image with appropriate image quality, automatic exposure control (AEC) for controlling exposure of an X-ray image is performed. The AEC is to control an irradiation amount of X rays emitted by an X-ray source such that a cumulative value of doses (cumulative dose) of X rays which are applied from the X-ray source, are transferred through a subject, and arrive at the X-ray image detection device, becomes a target dose (dose target value).

The cumulative dose of X rays is defined by a tube current-time product (mAs value) of an irradiation time (s: seconds) of X rays, and a tube current (mA) regulating a dose of X rays per unit time applied by the X-ray source. As a radiographing condition such as an irradiation time or a tube current, there are general recommended values depending on a radiographed part (a chest, a head, or the like), the sex, the age, and the like of a subject; however, the transfer of X rays is changed depending on individual differences such as a subject's constitution, and thus a dose of X rays arriving at the X-ray image detection device varies depending on subjects even if an irradiation amount from the X-ray source is the same. For this reason, the AEC is performed in order to obtain a dose target value without depending on individual differences such as a subject's constitution. In addition, the AEC is performed, and thereby a subject can be prevented from being exposed to excessive X rays.

In the X-ray radiographing system disclosed in JP2008-086358A, a dose detection sensor which detects a dose of X rays arriving at the X-ray image detection device is provided, and the AEC is performed based on a dose detected by the dose detecting sensor. JP2008-086358A discloses two AEC methods.

The first method is a method in which irradiation of X rays in one radiographing is performed so as to be divided into two irradiations of a pre-irradiation and a main irradiation, a dose of X rays per unit time arriving at the X-ray image detection device is measured by the dose detection sensor in the pre-irradiation, a dose of X rays to be applied in the main irradiation is determined based on the measured value, and X rays are applied at the determined dose. In the main irradiation, since a dose is determined in advance, the X-ray generation device starts irradiation at a tube current and an irradiation time set in advance, measures the irradiation time using a timer, and stops the irradiation at a time point reaching a set irradiation time.

The second method is a method in which a cumulative dose is measured in real time by the dose detection sensor during irradiation of X rays, whether or not the cumulative dose reaches a dose target value is determined, and irradiation from the X-ray source stops at a time point when the cumulative dose reaches the dose target value. In the second method, the X-ray generating device transmits a stop signal for stopping irradiation of X rays at a time point when a cumulative dose of X rays arriving at the X-ray image detection device reaches a dose target value. When the stop signal is received, the X-ray generation device stops the irradiation of X rays.

According to the first method, since, by performing the pre-irradiation, a dose per unit time corresponding to a subject's constitution is measured and a dose in the main irradiation is determined based on the measured value, an appropriate dose corresponding to the subject's constitution can be applied in the main irradiation. According to the second method, since a cumulative dose is measured in real time during the main irradiation, and irradiation of X rays stops at a time point when the cumulative dose reaches a dose target value, an appropriate dose corresponding to the subject's constitution can be applied in the main irradiation. In addition, in a case of the second method, a cumulative dose is measured in real time during the irradiation of X rays, and thus the pre-irradiation may be unnecessary.

SUMMARY OF THE INVENTION

The first method has a problem in that the pre-irradiation is necessary and thus a subject undergoes an unnecessary exposure accordingly. On the other hand, in the second method, the pre-irradiation is not performed, and thus there is no concern that a subject undergoes an unnecessary exposure due to the pre-irradiation.

However, in the second method, since AEC is performed during irradiation of X rays, in a case where the AEC process is delayed, a cumulative dose exceeds a dose target value and thus an excessive dose is generated. Therefore, there is a problem in that image quality of an X-ray image deteriorates or a subject undergoes an unnecessary exposure due to the excessive dose.

In other words, in the second method, the X-ray radiographing device performs a series of processes regarding AEC of measuring a cumulative dose during the irradiation of X rays, determining whether or not the cumulative dose reaches a dose target value, and transmitting a stop signal to the X-ray generation device at a time point when the cumulative dose reaches the dose target value. If the AEC processes are delayed, the timing for stopping the irradiation of X rays in the X-ray generation device also becomes late. Since the irradiation of X rays is continued until the irradiation of X rays stops after the cumulative dose reaches the dose target value, a dose of X rays applied during that time entirely becomes an excessive dose exceeding the dose target value. The later the timing for stopping the irradiation, the larger the excessive dose, and thus great influence is exerted on deterioration in image quality of an X-ray image or an exposure dose of a subject.

In a series of processes of the AEC, the greatest concern is a time lag in the transmission process of a stop signal. As causes of the time lag of communication, there is reduction in a communication rate or communication failure such as instantaneous interruption of a communication path. Particularly, in a case where a communication path of a stop signal from the X-ray radiographing device to the X-ray generation device is entirely or partially wireless, there is a frequent occurrence of a situation in which a communication rate is reduced or the communication path is instantaneously interrupted due to an electric wave state. In addition, when a wired manner is compared with a wireless manner, an occurrence frequency or an extent of communication failure is low, and communication quality is relatively stable. However, even in the wired manner, in a case where a relay device such as a switching hub or a router is interposed in the middle of the communication path, there is concern that, when a process load on the relay device is large, a communication rate is reduced, or when the relay device is frozen, the communication path is instantaneously interrupted.

Since an irradiation time in X-ray radiographing is very short, for example, about 60 ms in chest radiographing, a process time for the AEC is also very short, and, accuracy of the millisecond unit is obtained in the AEC. For this reason, influence of a delay of the AEC process caused by a time lag of communication is difficult to disregard, and there is a demand for countermeasures. JP2008-086358A discloses neither a problem that the timing for stopping irradiation of X rays is late due to a delay of an AEC process nor a solution thereto.

The present invention has been made in view of the above-mentioned problems and an object of the present invention is to provide a radiographic device, a radiographic system, and a control method and a recording medium for the radiographic device, capable of reducing an excessive dose caused by a delay of timing for stopping irradiation of radiation in a case of performing AEC of measuring a dose during irradiation of radiation and stopping the irradiation of radiation.

According to an embodiment of the present invention, there is provided a radiographic device which is connected to a radiation generation device irradiating a subject with radiation in order to allow communication therebetween and receives the radiation transferred through the subject so as to radiograph a radiological image of the subject, including an image detection unit that has an imaging region where a plurality of pixels accumulating signal charges corresponding to a dose of the radiation are arranged and detects the radiological image; a dose detection unit that detects an arrival dose of the radiation arriving at the imaging region; a stop timing prediction unit that predicts a stop timing for stopping irradiation of the radiation in the radiation generation device based on the arrival dose detected by the dose detection unit and a preset dose target value; and a communication unit that sends a stop timing notification for notifying the stop timing to the radiation generation device before the stop timing arrives.

The communication unit preferably sends the stop timing notification a predetermined time before the stop timing, the predetermined time being set in consideration of a time lag of communication with the radiation generation device.

The time lag of the communication is preferably an average time lag according to a communication path with the radiation generation device.

The stop timing notification preferably includes a scheduled stop time when a cumulative dose which is a cumulative value of the arrival dose is predicted to reach the dose target value.

The stop timing notification preferably includes a remaining time from a reference time point to a time point when the cumulative dose is predicted to reach the dose target value.

The stop timing notification preferably includes a sending time when the communication unit sends the stop timing notification, or an arrival time in the radiation generation device, set in consideration of a time lag of the communication, in addition to the remaining time.

The communication unit preferably sends the plurality of stop timing notifications until the stop timing arrives.

The dose detection unit preferably continuously detects a dose until a cumulative dose which is a cumulative value of the arrival dose reaches the dose target value.

The communication unit preferably sends the plurality of stop timing notifications until the cumulative dose reaches the dose target value.

The stop timing prediction unit preferably performs prediction again when the stop timing notification is sent.

The radiographic device preferably further includes a clock circuit that clocks the current time; and a synchronization unit that synchronizes the clock circuit with a clock circuit of the radiation generation device.

The communication unit preferably corrects the predetermined time set in consideration of a time lag of the communication based on the kind of the radiation generation device and a radiographing condition for driving the radiation generation device.

The communication unit and the radiation generation device are preferably directly connected to each other without interposing a relay device in a communication path therebetween.

A communication path between the communication unit and the radiation generation device may be entirely or partially wireless.

The communication unit may be a wireless communication unit. In this case, preferably, the wireless communication unit can send the stop timing notification using a plurality of wireless channels.

The stop timing prediction unit preferably corrects the predetermined time set in consideration of a time lag of the communication based on a time from when the communication unit sends a signal to the radiation generation device until the communication unit receives a response to the signal.

The stop timing notification preferably includes an error flag which is given by a communication device, including the communication unit, present in a communication path between the communication unit and the radiation generation device.

The radiographic device preferably further includes a gain setting unit that sets a gain when the radiological image is read from the image detection unit based on the arrival dose detected by the dose detection unit.

The dose detection unit is preferably provided in the imaging region of the image detection unit.

According to another embodiment of the present invention, there is provided a radiographic system including a radiation generation device that irradiates a subject with radiation; and a radiographic device that is connected to the radiation generation device in order to allow communication therebetween and receives the radiation transferred through the subject so as to radiograph a radiological image of the subject. The radiographic device includes an image detection unit that includes an imaging region where a plurality of pixels accumulating signal charges corresponding to a dose of the radiation are arranged and detects the radiological image; a dose detection unit that detects an arrival dose of the radiation arriving at the imaging region; a stop timing prediction unit that predicts a stop timing for stopping irradiation of the radiation in the radiation generation device based on the arrival dose detected by the dose detection unit and a preset dose target value; and a communication unit that sends a stop timing notification for notifying the radiation generation device of the stop timing to the radiation generation device before the stop timing arrives. The radiation generation device includes a radiation source that applies the radiation; and a radiation source control unit that controls the radiation source. The radiation source control unit includes a communication unit that receives the stop timing notification; and a control unit that stops irradiation by the radiation source based on the stop timing notification.

Preferably, the stop timing notification includes a scheduled stop time when a cumulative dose which is a cumulative value of the arrival dose is predicted to reach the dose target value, and the control unit stops the irradiation by the radiation source based on arrival of the scheduled stop time.

Preferably, the stop timing notification includes a remaining time from a reference time point to a time point when the cumulative dose is predicted to reach the dose target value, and the control unit stops the irradiation by the radiation source based on the remaining time having elapsed.

The communication unit preferably sends the plurality of stop timing notifications until the stop timing arrives. In addition, in a case where a plurality of stop timing notifications are sent, the control unit preferably stops the irradiation by the radiation source based on the latest stop timing notification of the plurality of stop timing notifications which have been received.

According to still another embodiment of the present invention, there is provided a control method for a radiographic device which is connected to a radiation generation device irradiating a subject with radiation in order to allow communication therebetween and includes an image detection unit provided with an imaging region where a plurality of pixels accumulating signal charges corresponding to a dose of the radiation are arranged and receiving the radiation transferred through the subject so as to detect a radiological image of the subject, including a dose detection step of detecting an arrival dose of the radiation arriving at the imaging region; a stop timing prediction step of predicting a stop timing for stopping irradiation of the radiation in the radiation generation device based on the detected arrival dose and a preset dose target value; and a communication step of sending a stop timing notification for notifying the radiation generation device of the stop timing to the radiation generation device before the stop timing arrives.

According to still another embodiment of the present invention, there is provided a non-transitory computer readable recording medium recording thereon a control program for a radiographic device which is connected to a radiation generation device irradiating a subject with radiation in order to allow communication therebetween and includes an image detection unit provided with an imaging region where a plurality of pixels accumulating signal charges corresponding to a dose of the radiation are arranged and receiving the radiation transferred through the subject so as to detect a radiological image of the subject, the control program causing a computer to function as a dose detection unit that detects an arrival dose of the radiation arriving at the imaging region; a stop timing prediction unit that predicts a stop timing for stopping irradiation of the radiation in the radiation generation device based on the arrival dose detected by the dose detection unit and a preset dose target value; and a communication unit that sends a stop timing notification for notifying the radiation generation device of the stop timing to the radiation generation device before the stop timing arrives.

According to the present invention, since a stop timing notification is sent to the radiation generation device before a stop timing arrives, even in a case where an AEC process delay occurs such as a delay of communication between the radiographic device and the radiation generation device, irradiation of radiation can stop around the stop timing, and thus an excessive dose caused by a delay of timing for stopping the irradiation of radiation can be reduced.

BRIEF DESCRIPTION OF THE DRAWINGS

FIG. 6 is a diagram illustrating a selection state of short-circuited pixels used for AEC or the like.

DESCRIPTION OF THE PREFERRED EMBODIMENTS

First Embodiment

Figure 1:
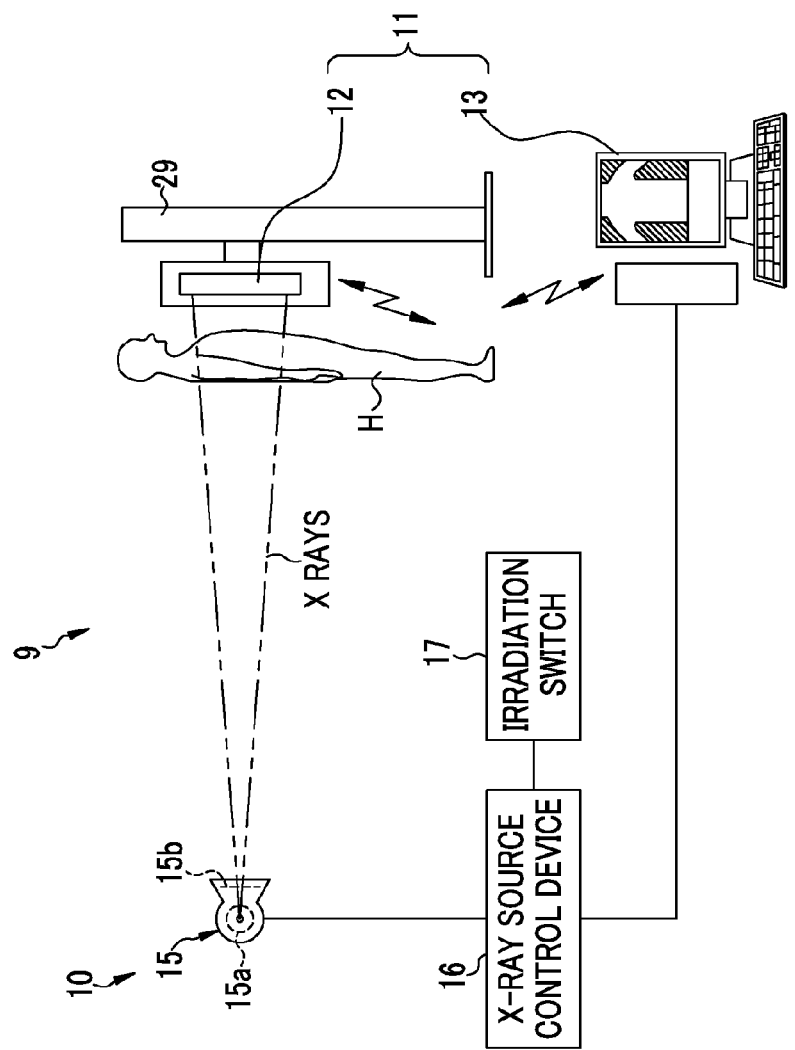
FIG. 1 is a diagram illustrating a schematic configuration of an X-ray radiographing system.

As illustrated in FIG. 1, an X-ray radiographing system 9 of the present invention includes an X-ray generation device (radiation generation device) 10 which generates X rays, and an X-ray radiographing device (radiographic device) 11 which receives X rays transferred through a subject H and radiographs an X-ray image of the subject H. The X-ray radiographing device 11 includes an electronic cassette 12 which detects an X-ray image, and a console 13 which controls the electronic cassette 12 and performs an image process on an X-ray image. In the X-ray radiographing system 9 of the present embodiment, the X-ray generation device 10 and the console 13 are connected so as to communicate with each other in a wired manner using a communication cable, and the electronic cassette 12 and the console 13 are connected so as to communicate with each other in a wired manner using electric waves. In addition, the console 13 is not essential, and the X-ray radiographing device 11 may be individually formed by the electronic cassette 12. Further, the electronic cassette 12 and the X-ray generation device 10 may directly communicate with each other in a wireless manner.

The X-ray generation device 10 includes an X-ray source 15, an X-ray source control device 16 controlling the X-ray source 15, and an irradiation switch 17 which is operated by an operator such as a radiographer and is used to instruct the X-ray source control device 16 to start irradiation of X rays.

The X-ray source 15 has an X-ray tube 15a which radiates X rays and a beam limiting device (collimator) 15b which limits an irradiation field of X rays. The X-ray tube 15a has a cathode formed by a filament emitting thermoelectrons and an anode (target) which radiates X rays when the emitted thermoelectrons strike against the anode. The beam limiting device 15b is one in which, for example, four lead plates shielding X rays are disposed on the respective sides of the rectangular shape, and a rectangular irradiation opening through which X rays are transferred is formed at the center thereof. The positions of the lead plates are moved so as to vary the size of the irradiation opening, thereby limiting an irradiation field.

Figure 2:
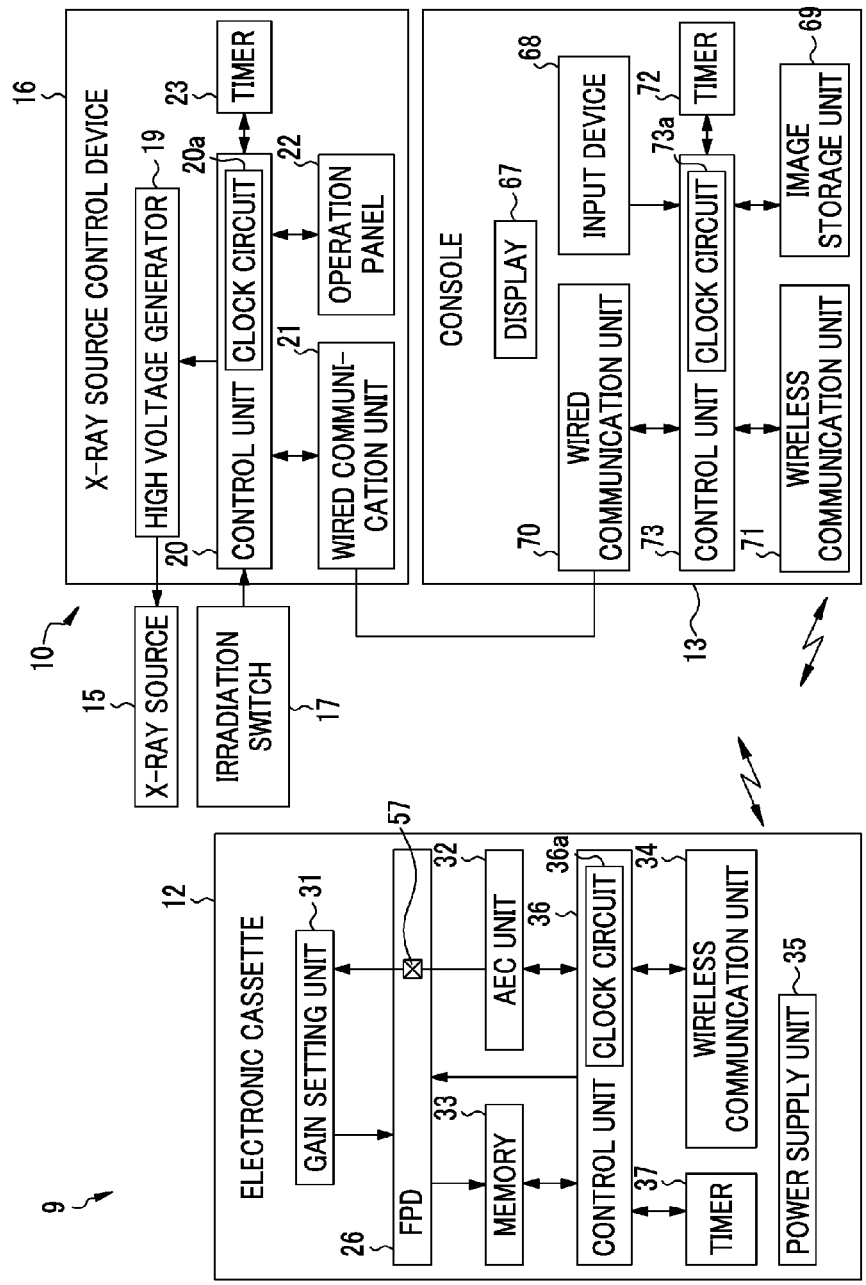
FIG. 2 is a block diagram illustrating a configuration of each device forming the X-ray radiographing system.

As illustrated in FIG. 2, the X-ray source control device 16 includes a high voltage generator 19 which supplies a high voltage (tube voltage) to the X-ray source 15, a control unit 20 which controls a tube voltage and a tube current supplied from the high voltage generator 19 to the X-ray source 15, an irradiation time of X rays, and the like, and a wired communication unit 21 which communicates with the console 13. The tube voltage determines radiation quality (energy spectrum) of X rays applied from the X-ray source 15, and the tube current determines a dose of X rays per unit time. The high voltage generator 19 generates a high tube voltage by boosting an input voltage using a transformer, and supplies driving power to the X-ray source 15 via a high voltage cable. In addition, in the present embodiment and the following embodiments, a communication unit includes both a wired communication unit and a wireless communication unit.

The wired communication unit 21 is connected to the console 13 via the communication cable. The radiographing conditions such as a tube voltage, a tube current and an irradiation time are input from the console 13 via the wired communication unit 21. The control unit 20 sets a driving condition of the X-ray source 15 based on the input radiographing conditions input from the console 13. In addition, the radiographing conditions may be input from an operation panel 22 provided in the X-ray source control device 16.

The irradiation switch 17 is connected to the control unit 20 of the X-ray source control device 16 via a signal cable. The irradiation switch 17 is, for example, a button switch on which a two-step pressing operation can be performed, and generates a warm-up start signal for starting warming up of the X-ray source 15 in the first-step pressing operation, and generates an irradiation start signal for starting irradiation of X rays by the X-ray source 15 in the second-step pressing operation. The warm-up start signal and the irradiation start signal generated by the irradiation switch 17 are input to the control unit 20 via the signal cable.

The irradiation of X rays by the X-ray source 15 is performed while the second-step pressing operation for the irradiation switch 17 is performed. In addition, in order to immediately stop the irradiation of X rays in an emergency, the irradiation of X rays stops when the second-step pressing operation of the irradiation switch 17 is cancelled. In addition, an operation switch may be provided in the console 13, and operation signals such as an irradiation start signal may be input to the X-ray source control device 16 from the console 13. In this case, the irradiation switch 17 may be omitted.

When the warm-up start signal is received from the irradiation switch 17, the control unit 20 starts warming up the X-ray source 15 via the high voltage generator 19. The control unit 20 issues an irradiation start command to the high voltage generator 19 when receiving the irradiation start signal from the irradiation switch 17. When the irradiation start command is received, the high voltage generator 19 applies a high voltage to the X-ray source 15 so as to start supplying power. When the power starts being supplied, the X-ray source 15 starts irradiation of X rays. In addition, in a case of stopping the irradiation of X rays, the control unit 20 issues an irradiation stop command to the high voltage generator 19. When the irradiation stop command is received, the high voltage generator 19 stops supplying power to the X-ray source 15 so as to stop the irradiation by the X-ray source 15.

The control unit 20 is provided with a clock circuit 20a which clocks the current time. In addition, the control unit 20 is connected to a timer 23 for measuring elapsing of set time. The timer 23 is operated by a command from the control unit 20. In a case where an irradiation time is set in advance as a radiographing condition, and radiographing is performed according to the set time, the control unit 20 sets the irradiation time in the timer 23 before starting irradiation of X rays, and starts clocking of the timer 23 at the same time as starting irradiation of X rays. In addition, the control unit 20 monitors the timer 23 after starting the irradiation of X rays, and issues an irradiation stop command at a time point when the irradiation time has elapsed so as to stop the irradiation by the X-ray source 15.

In addition, as described later, the X-ray radiographing system 9 can perform radiographing while executing AEC during the irradiation of X rays without setting an irradiation time in advance as a radiographing condition. In a case of performing radiographing while executing the AEC, the X-ray radiographing device 11 executes the AEC, and predicts a stop timing when the irradiation of X rays stops during the irradiation of X rays. The X-ray radiographing device 11 sends a stop timing notification for notifying the X-ray generation device 10 of the stop timing. In a case of performing radiographing while executing the AEC, the control unit 20 stops the irradiation of X rays based on the stop timing regulated in the stop timing notification. The stop timing is regulated in a form of a time point when irradiation is to be stopped or a remaining time of an irradiation time. The clock circuit 20a or the timer 23 is used to determine whether or not the stop timing arrives.

In addition, the control unit 20 has a system timer (not shown) embedded therein separately from the timer 23. Even in a case of performing the AEC, the control unit 20 sets the maximum irradiation time which is set with regard to the safety regulations of the X-ray source 15 in the system timer, and unconditionally stops irradiation of X rays in a case where the maximum irradiation time has elapsed. Thereby, the safety is secured in a case where a stop timing notification cannot be received from the X-ray radiographing device 11 due to failure or the like of the X-ray radiographing device 11. In addition, in a case of performing the AEC, an irradiation time set in the system timer may not be the maximum irradiation time with regard to the safety regulations. However, even in this case, a value with a margin is set in order to prevent irradiation of X rays from stopping before a stop timing notification is received although the X-ray radiographing device 11 is normally operated and sends the stop timing notification. For example, time obtained by adding a margin to a generally recommended value which is defined according to a radiographed part may be set.

Figure 3:
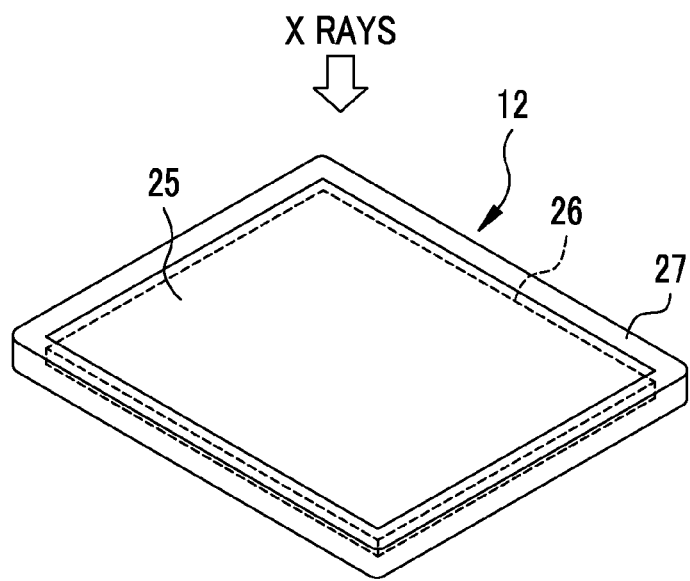
FIG. 3 is a perspective view illustrating an exterior of an electronic cassette.

As illustrated in FIG. 3, the electronic cassette 12 includes an FPD (image detection unit) 26 detecting an X-ray image based on X rays which are transferred through the subject H and are applied to an irradiation surface 25, and a portable casing 27 containing the FPD 26. The casing 27 has a flat form in which a planar shape is an approximately rectangular shape, and the planar size thereof is the substantially the same as the size of a film cassette or an IP cassette. A battery supplying power to the electronic cassette 12 is installed in a surface on an opposite side to the irradiation surface 25 of the casing 27.

As illustrated in FIG. 1, the electronic cassette 12 is set in a standing type radiography platform 29 facing the standing subject H, or in a lying radiography platform where the subject H can lie, and is used to radiograph an X-ray image. The radiography platform 29 may be used only for the electronic cassette 12, or may use a radiography platform of a film cassette or an IP cassette. In addition, in a case where a part which is difficult to radiograph is radiographed in a state where the electronic cassette 12 is set in the radiography platform, radiographing may be performed by placing the electronic cassette 12 on a bed or by allowing the subject H to hold the electronic cassette 12. Further, the electronic cassette 12 may not be substantially the same size as that of the IP cassette, and may have a portable size.

As illustrated in FIG. 2, the electronic cassette 12 includes, in addition to the FPD 26, a gain setting unit 31 which sets a value of the gain for amplifying a voltage signal indicating an X-ray image when the X-ray image is read from the FPD 26, an AEC unit 32 which performs AEC during irradiation of X rays, a memory 33 which stores image data of the X-ray image output from the FPD 26, a wireless communication unit 34 which communicates with the console 13, a power supply unit 35 which supplies power to each unit of the electronic cassette 12 from the above-described battery, a control unit 36 which controls the overall electronic cassette 12, and a timer 37 which measures the current time.

In addition, in this example, the electronic cassette 12 and the console 13 are connected so as to communicate with each other in a wireless manner; however, the electronic cassette 12 and the console 13 may be connected so as to communicate with each other in a wired manner. In this case, the electronic cassette 12 is provided with a wired communication unit instead of the wireless communication unit 34. In addition, in a case of being connected in a wired manner, power may be supplied to the electronic cassette 12 via a cable connected to the console 13. In a case of being connected in a wired manner as such, the battery or the wireless communication unit 34 may not be provided in the electronic cassette 12. Of course, a wired communication unit may be provided in the electronic cassette 12 in addition to the battery or the wireless communication unit 34, and selective switching between connection in a wireless manner and connection in a wired manner may be performed.

Figure 4:
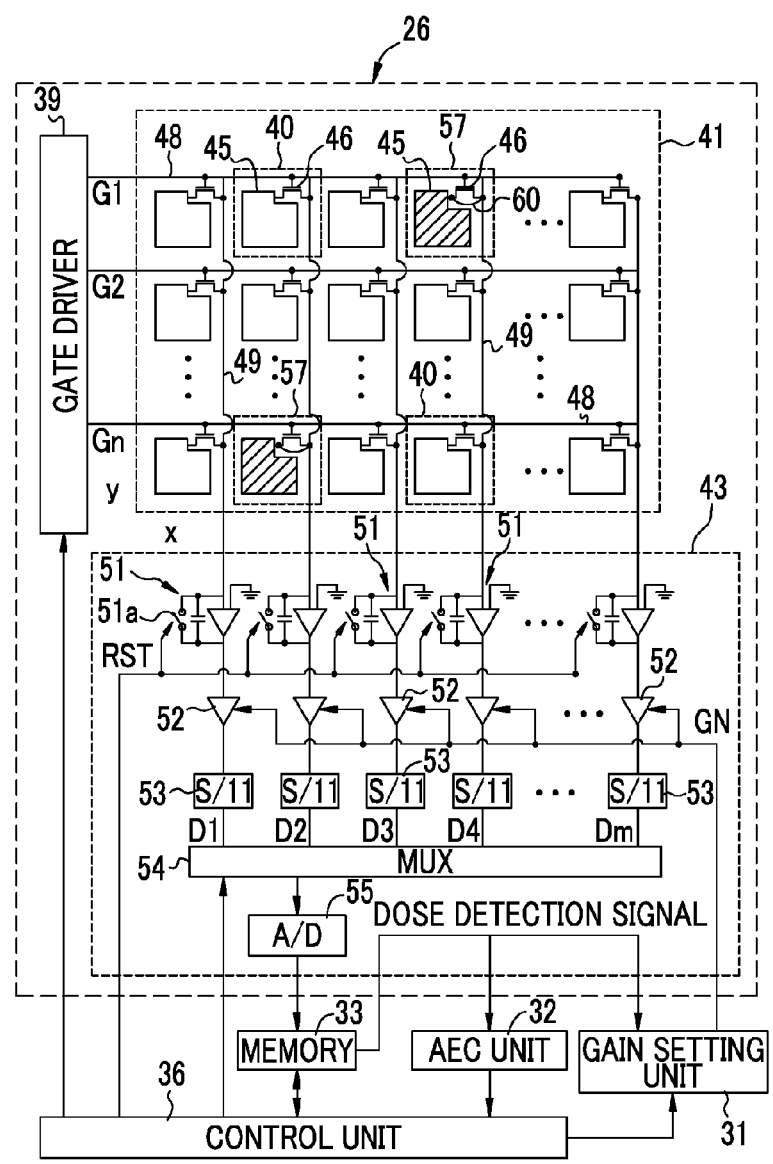
FIG. 4 is a block diagram illustrating a configuration of an FPD.

As illustrated in FIG. 4, the FPD 26 includes a detection panel having an imaging region 41 where a plurality of pixels 40 which accumulate signal charges corresponding to incidence amounts of X rays are arranged on a TFT active matrix substrate, a gate driver 42 which drives the pixels 40 and controls reading of signal charges, and a signal processing circuit 43 which converts the signal charges read from the pixels 40 into digital image data which is output. A plurality of pixels 40 are arranged in a two-dimensional matrix of n rows (x direction)×m columns (y direction) with a predetermined pitch. Here, n and m are integers of 1 or more. The number of pixels of the FPD 26 is, for example, about 2000× about 2000. The gate driver 42 and the signal processing circuit 43 are controlled by the control unit 36.

The FPD 26 includes a scintillator (not shown) which converts X rays into visible light, and is of an indirect conversion type in which the visible light converted by the scintillator undergoes photoelectric conversion in the pixels 40. The scintillator is disposed so as to face the entire surface of the imaging region 41 on which the pixels 40 are arranged. The scintillator includes fluorescent substances such as CsI (cesium iodide) or GOS (gadolinium oxy-sulfide). In addition, a direct conversion type FPD using a conversion layer (amorphous selenium or the like) which directly converts X rays into charge may be employed.

Each of the pixels 40 includes a photodiode 45 which is a photoelectric conversion element generating charge (electron-hole pair) when visible light is incident, a capacitor (not shown) which accumulates a charge generated by the photodiode 45, and a thin film transistor (TFT) 46 which functions as a switching element.

The photodiode 45 has a semiconductor layer (for example, a PIN type) such as a-Si (amorphous silicon), and has an upper electrode and a lower electrode thereon and thereunder, respectively. In the photodiode 45, the TFT 46 is connected to the lower electrode and a bias line (not shown) is connected to the upper electrode.

A bias voltage is applied to the upper electrodes of the photodiodes 45 via the bias line in all the pixels 40 of the imaging region 41. An electric field is generated in the semiconductor layer of the photodiodes 45 by applying the bias voltage, charges (electron-hole pairs) generated in the semiconductor layers through photoelectric conversion are moved to the upper electrode and the lower electrode, one of which has a positive polarity and the other of which has a negative polarity, and then the charges are accumulated in the capacitors.

The TFT 46 has a gate electrode connected to a scanning line 48, a source electrode connected to a signal line 49, and a drain electrode connected to the photodiode 45. The scanning lines 48 and the signal lines 49 are arranged in a lattice shape. The scanning lines 48 are provided so as to correspond to the number of rows (n rows) of the pixels 40, and each scanning line 48 is a common line connected to a plurality of pixels 40 of each row. The signal lines 49 are provided so as to correspond to the number of columns (m columns) of the pixels 40, and each signal line 49 is a common line connected to a plurality of pixels 40 of each column. The respective scanning lines 48 are connected to the gate driver 42, and the respective signal lines 49 are connected to the signal processing circuit 43.

By driving the TFTs 46, the gate driver 42 performs an accumulation operation of accumulating signal charges corresponding to incidence amounts of X rays in the pixels 40, a reading operation of reading the signal charges from the pixels 40, and a reset operation of resetting the signal charges accumulated in the pixels 40. The control unit 36 controls the start timing of each of the above-described operations performed by the gate driver 42.

In the accumulation operation, the TFTs 46 are turned off, and signal charges are accumulated in the pixels 40 during that time. In the reading operation, the gate driver 42 sequentially generates gate pulses G1 to Gn for simultaneously driving the TFTs 46 of the same row, sequentially activates the scanning lines 48 one by one, and turns on the TFTs 46 connected to the scanning lines 48 by one row.

When the TFTs 46 corresponding to one row are turned on, signal charges respectively accumulated in the pixels 40 corresponding to one row are input to the signal processing circuit 43 via the respective signal lines 49. In the signal processing circuit 43, the signal charges corresponding to one row are respectively converted into voltages, and output voltages corresponding to the signal charges are respectively read as voltage signals D1 to Dm.

A dark current occurs in the semiconductor layer of the photodiode 45 regardless of whether or not X rays are incident thereto. A dark charge corresponding to the dark current is accumulated in the capacitor since the bias voltage is applied thereto. The dark charge is a noise component in image data, and thus the reset operation is performed in order to remove the dark charge. The reset operation is an operation of sweeping out the dark charges occurring in the pixels 40 from the pixels 40 via the signal lines 49.

The reset operation is performed, for example, in a sequential reset method of resetting the pixels 40 by one row. In the sequential reset method, in the same manner as in the reading operation of signal charges, the gate driver 42 sequentially generates gate pulses G1 to Gn for the scanning lines 48 one by one, and turns on the TFTs 46 of the pixels 40 by one row. While the TFTs 46 are turned on, dark charges are input to the signal processing circuit 43 from the pixels 40 via the signal lines 49.

In the reset operation, unlike in the reading operation, the signal processing circuit 43 does not read output voltages corresponding to the dark charges. In the reset operation, a reset pulse RST is output to the signal processing circuit 43 from the control unit 36 in synchronization with the generation of each of the gate pulses G1 to Gn. When the reset pulse RST is input to the signal processing circuit 43, a reset switch 51a of an integral amplifier 51 described later is turned on, and the input dark charge is reset.

Instead of the sequential reset method, a parallel reset method in which arranged pixels of a plurality of rows are set to one group, reset is performed in the groups, and dark charges of rows corresponding to the number of groups are swept out at the same time, or an all-pixel reset method of inputting gate pulses to all the rows and sweeping out dark charges of all the pixels, may be used. The reset operation can be made to be performed at high speed using the parallel reset method or the all-pixel reset method.

The signal processing circuit 43 includes integral amplifiers 51, amplifiers 52, S/H units 53, a MUX 54, an amplification and A/D converter 55, and the like. The integral amplifier 51 is connected to each of the signal lines 49 individually. The integral amplifier 51 includes an operational amplifier and a capacitor connected between input and output terminals of the operational amplifier, and one input terminal of the operational amplifier is connected to the signal line 49, and the other input terminal (not shown) thereof is connected to the ground. The integral amplifiers 51 integrate and convert signal charges input from the signal lines 49 into voltage signals D1 to Dm which are output.

The amplifier 52 is connected to an output terminal of the integral amplifier 51 of each column. The amplifiers 52 amplify the voltage signals D1 to Dm output by the integral amplifiers 51 with a gain of a set value. For example, the amplifier 52 is an amplifier which feeds back an output of an operational amplifier to an input side thereof and amplifies an input voltage so as to be output, and is a gain variable amplifier which can change a gain by varying a ratio of resistance values between an input resistor (not shown) connected to the input terminal of the operational amplifier and a feedback resistor (not shown) connected between the input terminal and the output terminal of the operational amplifier. A value of the gain of the amplifier 52 is changed by varying a resistance value of the input resistor or the feedback resistor using a gain control signal (GN) input from the gain setting unit 31.

The sample and hold (S/H) units 53 are connected to the output sides of the amplifiers 52, hold the voltage signals output by the amplifiers 52, and output the held voltage signals D1 to Dm to the MUX 54. The A/D converter 55 is connected to the output side of the MUX 54. The MUX 54 sequentially selects one S/H unit 53 from a plurality of S/H units 53, and serially inputs the voltage signals D1 to Dm output from the selected S/H units 53 to the A/D converter 55.

The A/D converter 55 converts the input analog voltage signals D1 to Dm of one row into digital pixel values respectively corresponding to signal levels so as to be output to a memory 33. In the memory 33, pixel values of one row are respectively correlated with coordinates in the imaging region 41 of the pixels 40 and are recorded as image data indicating an X-ray image of one row.

When the integral amplifiers 51 output the voltage signals D1 to Dm of one row, the control unit 36 outputs the reset pulse RST to the integral amplifiers 51 so as to turn on the reset switches 51a of the integral amplifiers 51. Thereby, the signal charges of one row accumulated in the integral amplifiers 51 are reset. When the integral amplifiers 51 are reset, a gate pulse of the next row is output from the gate driver 42, and signal charges of the pixels 40 of the next row start being read. This operation is sequentially repeated, and thus signal charges of the pixels 40 of all the rows are read.

When reading of all the rows is completed, image data indicating an X-ray image corresponding to one screen is recorded in the memory 33. The control unit 36 performs offset compensation for removing an offset component which is fixed pattern noise caused by individual differences of the FPD 26 or environments, or sensitivity compensation for compensating variations in the sensitivity of the respective photodiodes 45 or variations in output characteristics of the signal processing circuit 43, on the image data recorded in the memory 33. The image data is read from the memory 33, and is transferred to the console 13 by the wireless communication unit 34.

A clock circuit 36a which clocks the current time is provided in the control unit 36 in the same manner as in the control unit 20 of the X-ray source control device 16, and is connected to a timer 37 for measuring elapsing of a set time.

As indicated by the hatching in FIG. 4, a plurality of short-circuited pixels 57 are provided in the imaging region 41 of the FPD 26. The short-circuited pixel 57 is a dose detection unit which detects a dose (arrival dose) of X rays arriving at the imaging region 41 and outputs the detected dose as a dose detection signal. The dose detection signal is used for the gain setting unit 31 to set a gain of the amplifier 52 and for the AEC unit 32 to perform AEC.

In addition, the short-circuited pixel 57 is used for the electronic cassette 12 to self-detect that the X-ray source 15 starts irradiation of X rays (start of irradiation) and stops the irradiation of X rays (finish of irradiation). Thereby, the electronic cassette 12 synchronizes each timing of start of irradiation or finish of irradiation of X rays with an operation of the FPD 26.

The short-circuited pixel 57 has the photodiode 45 and the TFT 46 in the same manner as each of the pixels 40, and the photodiode 45 generates a signal charge corresponding to an incidence amount of X rays. In the short-circuited pixel 57, a structural difference from the pixel 40 is that the source and the drain of the TFT 46 is short-circuited as indicated by the connection line 60, and thus there is no switching function of the TFT 46 of the short-circuited pixel 57. Thereby, a signal charge generated by the photodiode 45 of the short-circuited pixel 57 leaks to the signal line at all times, and is input to the integral amplifier 51. The integral amplifier 51 outputs a voltage signal corresponding to the signal charge input from the short-circuited pixel 57 as a dose detection signal of the short-circuited pixel 57 in the same manner as a signal charge from the pixel 40. For this reason, a dose detection signal of the short-circuited pixel 57 can be read even while the pixels 40 accumulate signal charges. In addition, without connecting the source and the drain of the TFT 46 of the short-circuited pixel 57, the TFT 46 itself may not be provided in the short-circuited pixel 57 and the photodiode 45 may be directly connected to the signal line 49.

Figure 5:
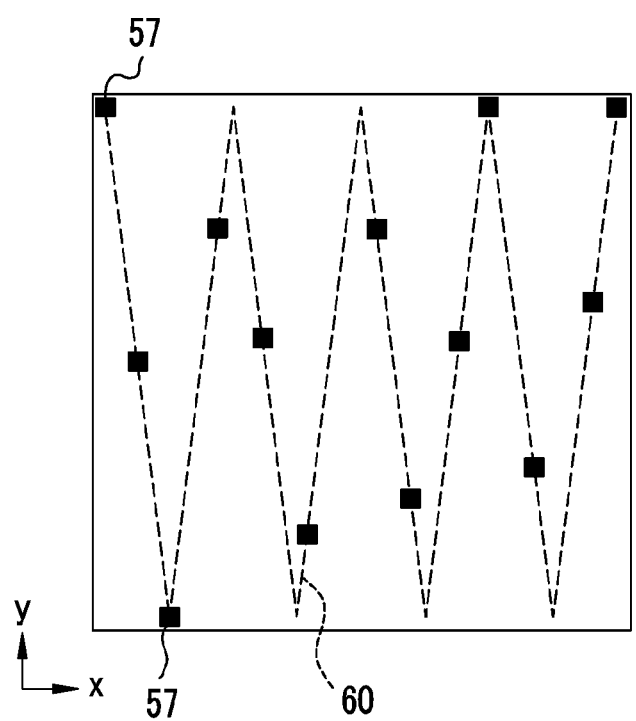
FIG. 5 is a diagram illustrating an arrangement state of short-circuited pixels.

As illustrated in FIG. 5, a plurality of short-circuited pixels 57 are distributed and disposed so as not to be biased locally in the imaging region 41, and are provided, for example, along the trajectory 60 of the waveform indicated by the dotted line which is symmetrical with respect to the center of the imaging region 41. The short-circuited pixel 57 is provided singly in a column of the pixels 40 connected to the same signal line 49, and the columns where the short-circuited pixels 57 are provided are disposed with two or three columns where the short-circuited pixels 57 are not provided, interposed therebetween. Positions of the short-circuited pixels 57 are known when the FPD 26 is manufactured, and the positions (coordinates) of all the short-circuited pixels 57 are stored in a nonvolatile memory (not shown) of the FPD 26 in advance. In addition, the arrangement of the short-circuited pixels 57 illustrated here is an example, and may be appropriately modified.

The control unit 36 selects the S/H unit 53 of the column to which the short-circuited pixel 57 is connected using the MUX 54, and reads a dose detection signal of the short-circuited pixel 57 output by the integral amplifier 51. The dose detection signal is input to the A/D converter 55 in a form of an analog voltage signal, and thus the A/D converter 55 converts the dose detection signal into a digital value which is output to the memory 33. The dose detection signal is recorded in the memory 33 so as to be correlated with coordinates of the short-circuited pixel 57. The control unit 36 resets the integral amplifier 51 when reading the dose detection signal from the integral amplifier 51. The control unit 36 repeatedly performs this dose detection operation at a very short interval relative to an irradiation time of X rays. A dose detection signal read by one dose detection operation is an instantaneous value of a dose of incident X rays. The dose detection signals recorded in the memory 33 are sequentially read by the control unit 36, the gain setting unit 31, and the AEC unit 32.

Before X-ray radiographing, a radiographing preparation instruction for instructing the electronic cassette 12 to prepare for radiographing is input to the electronic cassette 12 from the console 13. When the radiographing preparation instruction is received, the control unit 36 transitions from an idle state to a standby state of irradiation of X rays. In the standby state, the FPD 26 performs the reset operation at a predetermined interval. In addition, the control unit 36 starts the dose detection operation of the short-circuited pixel 57. In the dose detection operation, dose detection signals of all the short-circuited pixels 57 in the imaging region 41 are read at a predetermined sampling interval and are recorded in the memory 33.

The control unit 36 starts a start detection operation of detecting start of irradiation based on the sequentially recorded dose detection signals. In the start detection operation, the dose detection signals are read from the memory 33, and coordinates of a dose detection signal indicating the maximum value are specified. The control unit 36 adds a plurality of dose detection signals which are sequentially recorded in the memory 33 to the dose detection signal of the coordinates indicating the maximum value so as to obtain an integrated value. In addition, the integrated value is monitored, and start of irradiation is detected when the integrated value exceeds a predetermined start threshold value. In the start detection operation, the reason why a dose detection signal indicating the maximum value is specified is that the short-circuited pixel 57 which is an output source of the dose detection signal is considered as being in a location omission region which does not face the subject H in the imaging region 41 and to which X rays not being transferred through the subject H are incident, like the short-circuited pixel 57b in FIG. 6. The short-circuited pixel 57b of the location omission region is fast in rising of an output and thus can rapidly perform start detection.

When the start of irradiation is detected, the control unit 36 changes the FPD 26 from the reset operation to the accumulation operation. In addition, transition to a finish detection operation is performed in parallel to the accumulation operation. In the finish detection operation as well, a dose detection signal of the coordinates specified in the start detection operation is monitored, and finish of irradiation is detected at a time point when an output value of the dose detection signal decreases and is smaller than a predetermined finish threshold value. When the finish of irradiation is detected, the control unit 36 changes the FPD 26 from the accumulation operation to the reading operation.

In addition, a dose detection signal used for start detection or finish detection may be a dose detection signal of a single short-circuited pixel 57 indicating the maximum value, or may be a sum value, an average value, or the like of a plurality of short-circuited pixels 57 determined as being in the location omission region. The dose detection operation for the short-circuited pixel 57 is repeatedly performed until the finish of irradiation is detected.

Figure 6:
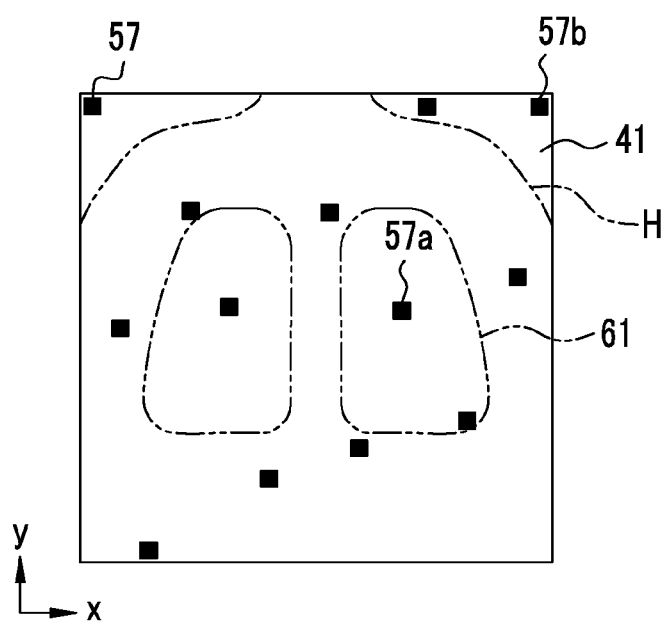

In addition, a radiographing condition is transferred to the electronic cassette 12 from the console 13 before the radiographing. The control unit 36 inputs information of a radiographed part from the input radiographing condition to the gain setting unit 31 and the AEC unit 32. The gain setting unit 31 and the AEC unit 32 set the short-circuited pixel 57 used for gain setting and AEC based on the information of the radiographed part. In a case of gain setting or AEC, for example, like a short-circuited pixel 57a in FIG. 6, the short-circuited pixel 57a which is positioned in a subject region facing the subject H in the imaging region 41 is selected. More specifically, in a case where the chest is designated as a radiographed part in the radiographing condition, as illustrated in FIG. 6, the short-circuited pixel 57a disposed in the lung field 61 which is a target region is selected as a short-circuited pixel for gain adjustment and AEC. For example, a plurality of short-circuited pixels 57a in the target region are set, and a sum value or an average value of outputs thereof is used.

The gain setting unit 31 and the AEC unit 32 selectively read a dose detection signal having coordinates set according to the radiographed part out of the dose detection signals in the memory 33.

The gain setting unit 31 determines a value of the gain for amplifying a voltage signal indicating an X-ray image in the reading operation of the X-ray image based on the dose detection signal. The gain setting unit 31 sequentially reads the dose detection signals from the memory 33 during irradiation of X rays, and adds the read dose detection signals so as to calculate a cumulative dose which is an integrated value of the doses. The short-circuited pixel 57 which is positioned in the target region is selected, and a cumulative dose of X rays which are incident to the short-circuited pixel 57 corresponds to a cumulative dose of X rays which are incident to the pixels 40 around the short-circuited pixel 57. The gain setting unit 31 determines a value of the gain in the reading operation of an X-ray image based on the calculated cumulative dose. The value of the gain determined by the gain setting unit 31 is set in the amplifier 52 using the gain control signal (GN).

The gain setting may be performed no later than the start of an operation of reading an X-ray image from the FPD 26. For this reason, the gain setting unit 31 may determine a gain based on a cumulative dose at the time when irradiation of X rays finishes or may determine a gain based on a cumulative dose during irradiation of X rays.

In addition, as described above, since the short-circuited pixel 57 positioned in the target region is selected, a cumulative dose of X rays which are incident to the short-circuited pixel 57 indicates a density of the target region in the X-ray image. In the X-ray image, to clearly visualize density gray-scales indicating shading changes of the target region is important. Since a dynamic range of the A/D converter 55 is limited, a value of the gain is adjusted so as for the shading changes of the target region to lie in the dynamic range of the A/D converter 55. Specifically, in a case where a cumulative dose (a density of the target region) is small, the gain increases, and in a case where a cumulative dose (a density of the target region) is large, the gain decreases. This gain adjustment may also be performed on the image data which is converted into digital values by the A/D converter 55, but, if the gain adjustment is performed on the image data converted into digital values, noise is also amplified, and thereby S/N is reduced. By performing the gain adjustment in the step of the analog signal, favorable S/N can be maintained.

In addition, although, in this example, an example of changing the gain of the amplifier 52 has been described, an integral amplifier of which the gain can be adjusted may be used as the integral amplifier 51, and the gain of the integral amplifier may be adjusted.

Figure 7:
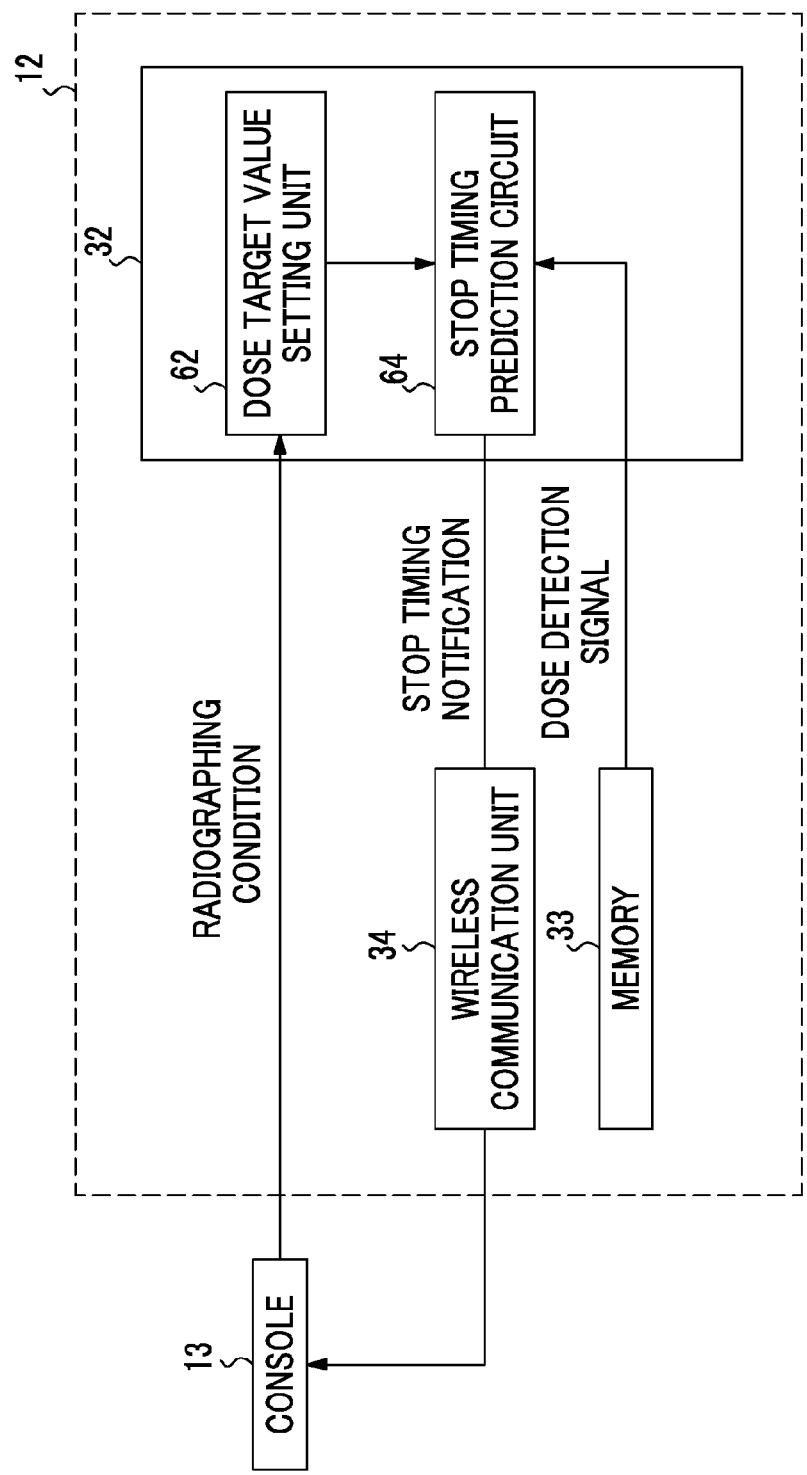
FIG. 7 is a block diagram illustrating a configuration of an exposure control unit.

As illustrated in FIG. 7, the AEC unit 32 includes a dose target value setting circuit 62 and a stop timing prediction circuit 64 (a stop timing prediction unit), and performs AEC based on a dose detection signal of the short-circuited pixel 57. The dose target value setting circuit 62 sets a dose target value which is a dose value of X rays required for detecting an X-ray image based on a radiographing condition transferred from the console 13. The dose target value is stored in a memory or the like (not shown) of the AEC unit 32, for example, in correlation with radiographing conditions such as a radiographed part, a tube voltage, and a tube current, and the AEC unit 32 selects a dose target value corresponding to input radiographing conditions. Alternatively, a dose target value may be recorded in a radiographing condition transferred from the console 13 in advance in correlation with a radiographed part, and the dose target value read from the radiographing condition may be set.

The dose target value refers to a dose in which an arrival dose at the imaging region 41 is sufficient to read an image. Since there is shading in an image, the dose target value is obtained an average value or an integrated value in the shading of an image sufficient to be read. In addition, the dose target value may be an average value or an integrated value in not the entire image but a target region in the image. The dose target value is an object for comparison with whether or not an irradiation amount of X rays measured using the short-circuited pixel 57 (dose detection unit) described later is sufficient, and thus a form of the dose target value is changed depending on whether values detected by a plurality of short-circuited pixels 57 are compared as an average value or are compared as an integrated value. The dose target value is a value which is determined for each hospital, for each radiographer, or for each doctor, or when the product is shipped, as a setting value. Alternatively, a dose target value may be determined according to a radiographed part. In addition, in a case of there is a single short-circuited pixel 57, naturally, an integrated value and an average value are the same value.

In the same manner as the gain setting unit 31, the stop timing prediction circuit 64 sequentially reads the dose detection signals from the memory 33, adds the read dose detection signals to each other, and calculates a cumulative dose which is an integrated value of the doses. The stop timing prediction circuit 64 starts calculating a cumulative dose at a time point when the start of irradiation is detected. In addition, a stop timing when the irradiation of X rays is required to stop in the X-ray generation device 10 is predicted based on the cumulative dose, the set dose target value, and an elapsed time until the cumulative dose is obtained. The stop timing is a scheduled stop time to when a cumulative dose of X rays applied to the FPD 26 is predicted to arrive at the dose target value. The elapsed time is measured by the timer 37.

Figure 8:
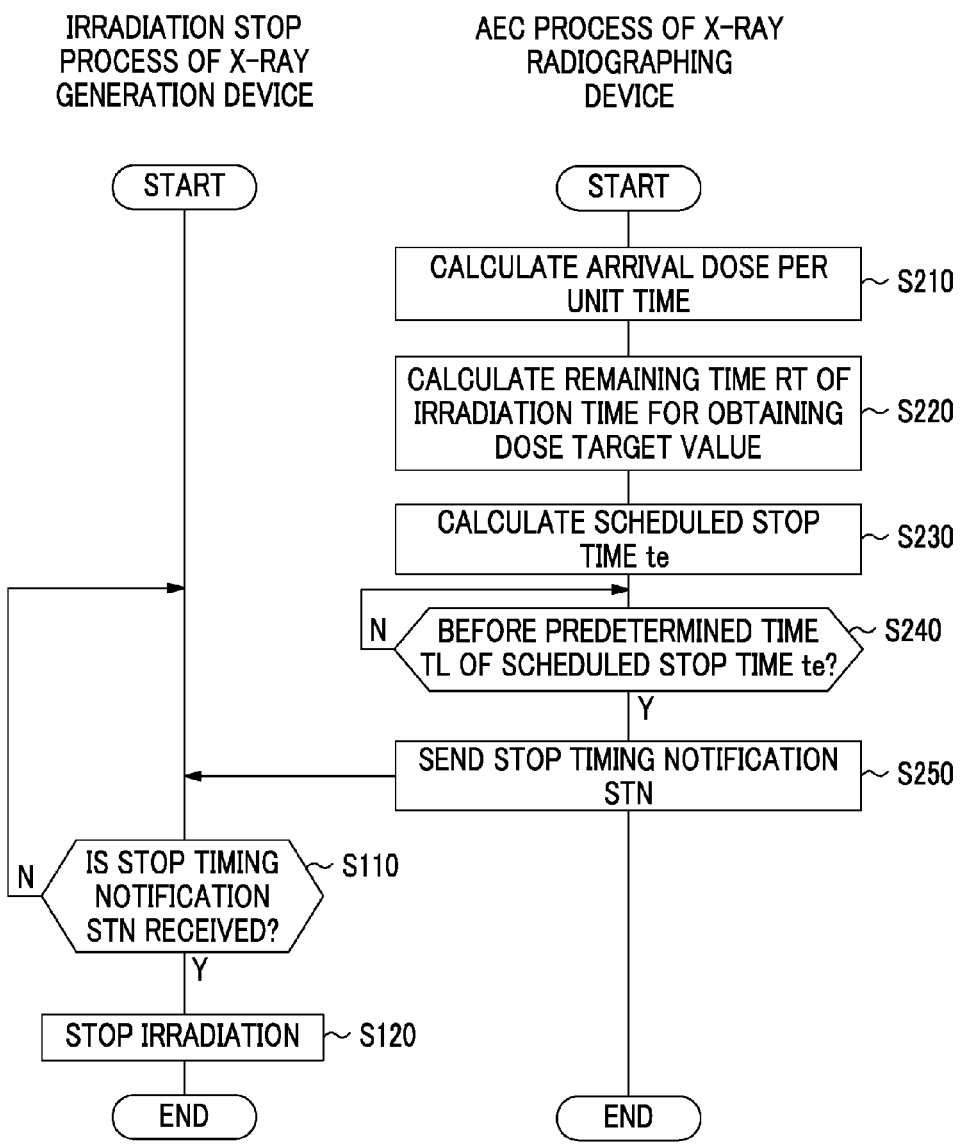
FIG. 8 is a flowchart illustrating procedures of an AEC process.

Specifically, as illustrated in FIG. 8, the stop timing prediction circuit 64 calculates a dose per unit time by dividing a calculated cumulative dose by an elapsed time until arriving at the cumulative dose at a predetermined timing during the irradiation of X rays (S210). This dose is an arrival dose of X rays arriving at a target region in the imaging region 41 for the elapsed time. In addition, a difference from the dose target value of X rays which have already been incident is obtained by subtracting the cumulative dose used to calculate the arrival dose per unit time from the dose target value. This difference is a dose required to obtain the dose target value, and a remaining time RT of the irradiation time required to obtain the dose target value is calculated by dividing the difference by the previously calculated dose per unit time (S220). The scheduled stop time te is calculated as a stop timing by adding the current time acquired from the clock circuit 36a to the remaining time RT (S230).

Figure 9:
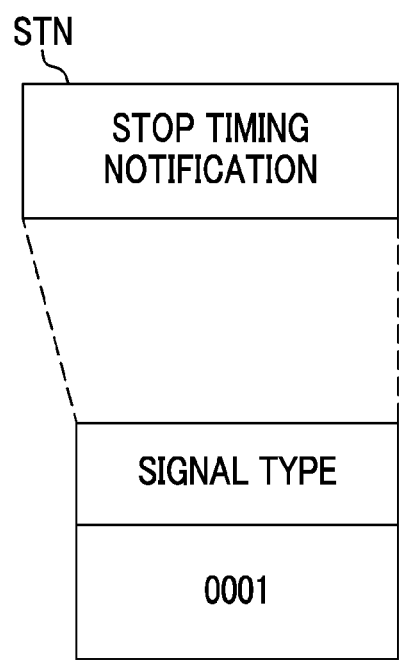
FIG. 9 is a diagram illustrating a data format of a stop timing notification according to a first embodiment.

The stop timing prediction circuit 64 generates a stop timing notification STN when calculating the scheduled stop time te. In FIG. 9 illustrating a data format of the stop timing notification STN, the stop timing notification STN of this example includes only a signal type ("0001") indicating that a signal is a stop timing notification as information. The stop timing prediction circuit 64 refers to the current time of the clock circuit 36a, and sends the stop timing notification STN for notifying the X-ray source control device 16 of the stop timing to the console 13 via the wireless communication unit 34 before a predetermined time TL of the scheduled stop time te (S240). The console 13 relays the stop timing notification STN received from the electronic cassette 12 so as to be transferred to the X-ray source control device 16.

When the stop timing notification STN is received (S110), the X-ray source control device 16 immediately outputs an X-ray irradiation stop command to the high voltage generator 19 so as to stop the irradiation of X rays by the X-ray source 15.

A timing for predicting the stop timing is, for example, a timing when a cumulative dose used for the prediction reaches an extent of a dose capable of securing prediction accuracy. As a method of regulating the timing, a time point when a predetermined time has elapsed from a time point when start of irradiation is detected may be used, or a time point when a cumulative dose reaches a predetermined threshold value may be used. Since an arrival dose is changed depending on a radiographed part, a predetermined time or a threshold value for regulating a timing when prediction is performed may be determined depending on a radiographed part.

In addition, in order to increase prediction accuracy, a plurality of predictions may be performed at a predetermined interval. In a case of performing a plurality of predictions, each cumulative dose may use a cumulative dose from start of irradiation at each prediction time point, or may use a cumulative dose after the previous prediction. An elapsed time for obtaining a dose per unit time is naturally selected depending on which cumulative dose is used. If the prediction accuracy increases, an error between a cumulative dose and a dose target value is reduced, and thus image quality of an X-ray image can be improved or an unnecessary exposure dose of the subject H can be reduced.

In addition, in this example, the dose detection operation starts after start of irradiation is detected and thus has no problem; however, in a case where the dose detection operation starts during the reset operation of the FPD 26, a dose detection signal output during the reset operation is not preferably used for calculating a cumulative dose. This is because the dose detection signal output during the reset operation is caused by a dark current of the FPD 26 and thus does not indicate an arrival dose of X rays.

In addition, the predetermined time TL in step S240 is, for example, an average communication time required to transmit the stop timing notification STN using a communication path from the electronic cassette 12 to the X-ray source control device 16 via the console 13. The predetermined time TL is time in which an average value of a time lag of communication is taken into consideration in a case of using the communication path during the communication time. In this example, the communication path is in a wireless manner between the electronic cassette 12 and the console 13 and in a wired manner between the console 13 and the X-ray source control device 16.

Since the wireless manner is not stable in communication quality as compared with the wired manner, reduction in a communication rate or instantaneous interruption of a communication path tends to occur depending on an electric wave state. For this reason, as compared with the wired manner, communication time and an average value of time lags of communication are also great. The wired manner is stable in communication quality as compared with the wireless manner, but communication time or an average value of time lags of communication is changed depending on there is a relay such as a switching hub or a router in the middle of a communication path. In addition, in this example, the console 13 is interposed in the communication path between the electronic cassette 12 and the X-ray source control device 16, and time required for the relay process in the console 13 is also taken into consideration when setting the predetermined time TL. The predetermined time TL is set in advance according to this configuration of the communication path. The predetermined time TL is stored in an internal memory of the control unit 36. The predetermined time TL may be stored in the console 13, and the electronic cassette 12 may acquire the predetermined time TL from the console 13.

In this example, a scheduled stop time te is calculated as the stop timing. For this reason, if a sending time of the stop timing notification STN from the electronic cassette 12 is put before the predetermined time TL of the scheduled stop time te, an arrival time of the stop timing notification STN at the X-ray source control device 16 is exactly the scheduled stop time te. Thereby, an excessive dose exceeding a dose target value, caused by a delay of timing for stopping irradiation of X rays, can be reduced. The excessive dose causes image quality of an X-ray image to deteriorate or an unnecessary exposure dose of a subject to increase, and this adverse influence is prevented by the present invention.

As illustrated in FIG. 2, the console 13 includes a display 67 which displays a radiographing order, an X-ray image, or the like, an input device 68 for inputting a radiographing condition or the like, an image storage unit 69 which stores image data of an X-ray image, a wired communication unit 70 which communicates with the X-ray source control device 16, a wireless communication unit 71 which communicates with the electronic cassette 12, a timer 72, and a control unit 73 which controls the overall console 13. The control unit 73 is provided with a clock circuit 73a in the same manner as the control unit 20 of the X-ray source control device 16 and the control unit 36 of the electronic cassette 12.

The control unit 73 of the console 13 receives an input of an examination order including information such as the sex and the age of a patient, a radiographed part, and a radiographing purpose, and displays the examination order on the display 67. The examination order is input from an external system which manages patient information or examination information related to a radiographic examination, such as an HIS (Hospital Information System) or an RIS (Radiology Information System) connected to the wired communication unit 70 or the wireless communication unit 71, or is manually input by an operator such as a radiographer using the input device 68. Radiographing conditions such as a tube voltage, a tube current, and a radiographed part is input to the console 13 by an operator using the input device 68 based on content of the examination order displayed on the display 67.

The control unit 73 transmits the radiographing conditions to the electronic cassette 12 and the X-ray source control device 16, and sets signal processing conditions of the FPD 26 such as the above-described dose target value in the electronic cassette 12. In addition, the control unit 73 relays the stop timing notification STN transferred to the X-ray source control device 16 from the electronic cassette 12. The console 13 immediately transmits the stop timing notification STN to the X-ray source control device 16 when receiving the stop timing notification STN.

The control unit 73 of the console 13 receives image data of an X-ray image transferred from the electronic cassette 12 and performs various image processes such as gamma compensation and a frequency process thereon. The X-ray image having undergone the image processes is displayed on the display 67 of the console 13, and, the data thereof is stored in the image storage unit 69 including a hard disk drive, or is stored in a data storage device such as an image accumulation server connected to the console 13 via a network.

Figure 10:
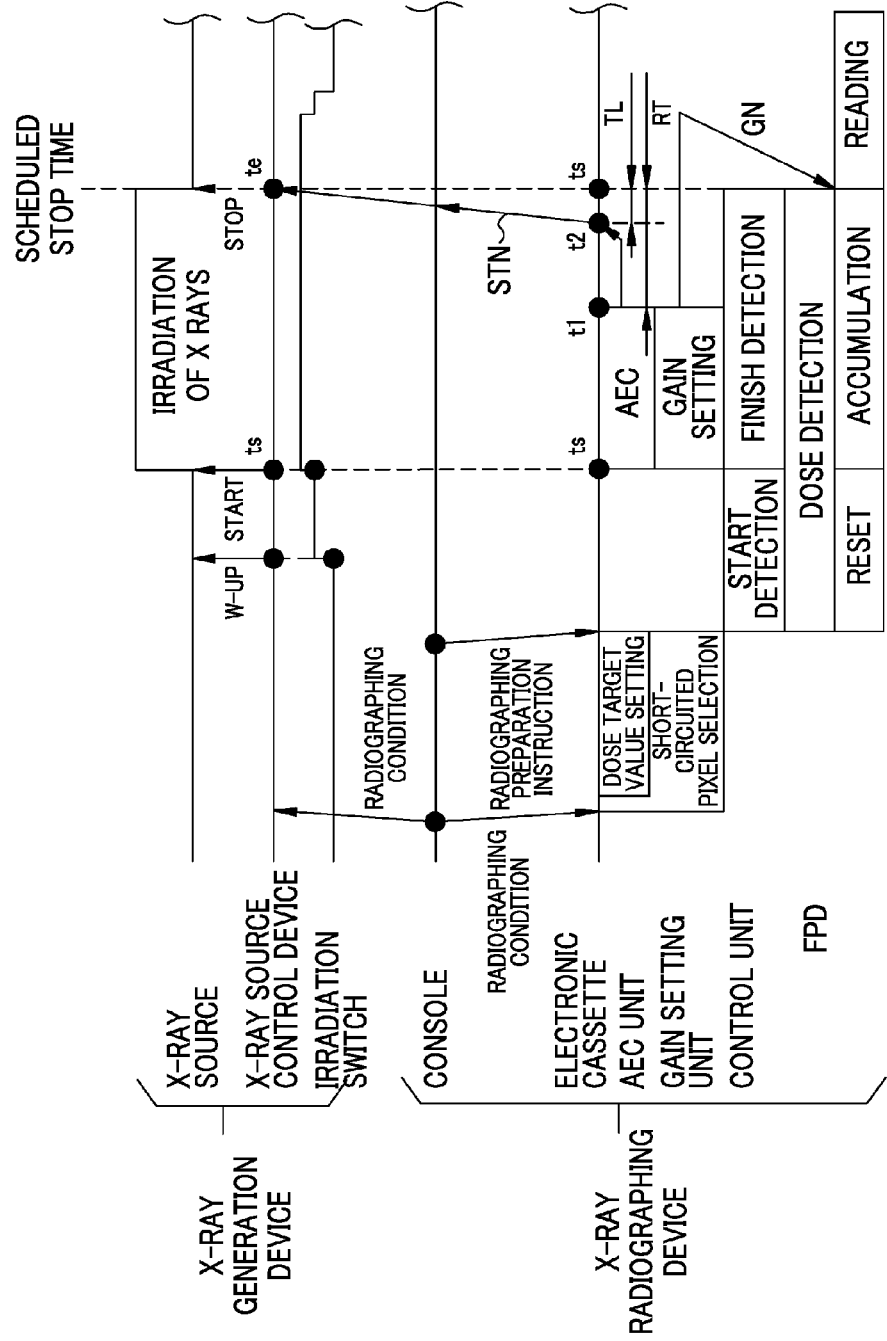
FIG. 10 is a flowchart illustrating an operation timing of each of the X-ray generation device and the X-ray radiographing device.

An operation of the X-ray radiographing system 9 will be described with reference to FIG. 8, and FIG. 10 which is a timing chart illustrating operation timings of the respective units of the X-ray generation device 10 and the X-ray radiographing device 11. A radiographed part of the subject H and an irradiation position of the X-ray source 15 are aligned with the radiography platform 29 in which the electronic cassette 12 is set. An examination order including information such as the sex and the age of a patient, a radiographed part, and a radiographing purpose is input to the console 13, and radiographing conditions are set based on this examination order. As illustrated in FIG. 10, the console 13 transmits the set radiographing conditions to the electronic cassette 12 and the X-ray source control device 16.

The control unit 20 of the X-ray source control device 16 sets driving conditions such as a tube voltage and a tube current of the X-ray source 15 based on the radiographing conditions received from the console 13. In this example, the X-ray radiographing system 9 performs radiographing while performing AEC, and thus the control unit 20 sets the maximum irradiation time with regard to the safety regulations in the system timer. In addition, the gain setting unit 31 and the AEC unit 32 of the electronic cassette 12 selects the short-circuited pixel 57 used for gain setting and the AEC based on the radiographing conditions received by the control unit 36 from the console 13. In addition, the AEC unit 32 sets a dose target value based on the radiographing conditions.

The console 13 transmits a radiographing preparing instruction signal for preparing for radiographing to the electronic cassette 12. When the radiographing preparation instruction signal is received, the electronic cassette 12 makes the FPD 26 transition to a standby state. The control unit 36 makes the FPD 26 start the reset operation and the dose detection operation. Further, the control unit 36 starts a start detection operation of detecting start of irradiation of X rays based on a dose detection signal acquired through the dose detection operation.

When a warm-up start signal is input by half-pressing the irradiation switch 17, the X-ray source control device 16 inputs a warm-up start command (W-UP) to the high voltage generator 19 so as to start warm-up of the X-ray source 15. In addition, when an irradiation start signal is input by full-pressing the irradiation switch 17, an irradiation start command (START) is input to the high voltage generator 19. Thereby, the X-ray source 15 starts irradiating the subject H with X rays.

When the irradiation of X rays starts, the X rays transferred through the subject H are incident to the FPD 26, and thus an output value of the dose detection signal from the short-circuited pixel 57 increases. The control unit 36 specifies a dose detection signal having the maximum output, regarded as being positioned in the location omission region, out of dose detection signals recorded in the memory 33. In addition, the control unit 36 obtains an integrated value of doses based on the dose detection signal, compares the integrated value with a start threshold value, and detects that the irradiation of X rays starts when the integrated value exceeds the start threshold value.

At the stop timing is when the start of irradiation is detected, the FPD 26 turns off the TFTs 46 of the pixels 40 so as to start the accumulation operation.

The gain setting unit 31 and the AEC unit 32 of the electronic cassette 12 start integrating a cumulative dose of the X rays which are incident to the target region on the basis of a dose detection signal output by the short-circuited pixel 57 selected based on the radiographed part. In addition, the gain setting unit 31 sets a gain in the amplifier 52 when a signal voltage of an X-ray image is read from the FPD 26, based on the cumulative dose until the reading operation starts. A gain control signal GN is input to the amplifier 52 and thus the gain thereof is adjusted.

The AEC unit 32 predicts a stop timing at the preset time point t1. In FIG. 8, an arrival dose per unit time at the prediction time point t1 based on a cumulative dose at the time point t1 and an elapsed time measured by the timer 37 (S210), and a remaining time RT of the irradiation time required to obtain the dose target value is calculated (S220). In addition, a scheduled stop time te is calculated by adding the remaining time RT to the current time (S230), and a stop timing notification STN is generated. In addition, in the present embodiment, the time point t1 is used as a reference time point.

In FIG. 10, the AEC unit 32 refers to the clock circuit 36a, waits until the time point t2 which is the predetermined time TL earlier than the scheduled stop time te, and sends the stop timing notification STN at the time point t2 (S240 of FIG. 8). The stop timing notification STN is transferred from the electronic cassette 12 to the X-ray source control device 16 via the console 13. The stop timing notification STN is sent before the predetermined time TL of the scheduled stop time te in consideration of a time lag of communication, and thus arrives at the X-ray source control device 16 at the scheduled stop time te. When the stop timing notification STN is received (S110 of FIG. 8), the X-ray source control device 16 immediately inputs an irradiation stop command (STOP) so as to stop the operation of the X-ray source 15 (S120 of FIG. 8).

The control unit 36 performs a finish detection operation and monitors an output of the short-circuited pixel 57 during the irradiation of X rays. When the stop command is input, the X rays start reducing the X-ray intensity. The control unit 36 detects that the irradiation of X rays finishes when the output of the short-circuited pixel 57 is smaller than a finish threshold value. The FPD 26 finishes the accumulation operation and starts the reading operation when the irradiation stop is detected. In this reading operation, the amplifier 52 amplifies the signal voltage indicating an X-ray image based on the gain set by the gain setting unit 31. Data of the X-ray image read from the FPD 26 is transferred from the electronic cassette 12 to the console 13, and is stored in the image storage unit 69 after undergoing predetermined image processes.

As described above, according to the present embodiment, the stop timing notification STN is sent to the X-ray source control device 16 from the electronic cassette 12 before the predetermined time TL of the scheduled stop time te, and the X-ray source control device 16 immediately stops irradiation of X rays when receiving the stop timing notification STN. The predetermined time TL is set inconsideration of a time lag of communication of the communication path between the electronic cassette 12 and the X-ray source control device 16, and thus the irradiation of X rays stops at the scheduled stop time te predicted in the electronic cassette 12.

The scheduled stop time te is to predict a time point when an arrival dose of X rays which are incident to the target region of the subject H reaches the dose target value. Since the irradiation of X rays stops at the scheduled stop time te, no excessive dose exceeding the dose target value is generated. For this reason, an excessive dose caused by a time lag of communication can be reduced as compared with the related art in which AEC is performed in the X-ray radiographing device 11, and a stop signal is sent to the X-ray generation device 10 at a time point when a cumulative dose reaches a dose target value. Since the excessive dose causes image quality of an X-ray image to deteriorate or an unnecessary exposure dose of the subject H to increase, an X-ray image with more favorable image quality than in the related art can be obtained by reducing the excessive dose. In addition, an exposure dose of the subject H is also reduced.

In addition, the wireless manner has lower communication quality or stability than the wired manner, and thus there is a great necessity for taking a time lag of communication into consideration. In a case where the communication path is entirely or partially in the wireless manner as in this example, the present invention is preferably useful.

In addition, the predetermined time TL is a value set in consideration of an average communication time or time lag, and thus a real communication time or time lag may be larger or smaller than the average value. In this case, although there is an error with a target stop timing, the stop timing notification STN is sent before a cumulative dose reaches a dose target value, and thus an error is small as compared with the related art in which the stop timing notification STN is sent after a cumulative dose reaches a dose target value.

In addition, the stop timing notification STN (FIG. 9) of this example includes only a signal type and does not include other pieces of information. For this reason, there is a merit in that any process of generation, transmission and reception and discrimination of the stop timing notification STN can be simplified in any one of a transmission side and a reception side, and thus device design is easy.

In this example, the X-ray generation device 10 immediately stops irradiation of X rays after receiving the stop timing notification STN, and thus whether or not the stop timing notification STN is received may be determined. For this reason, even a signal type as content of the stop timing notification STN may not be necessary. For example, information may not be included in the stop timing notification STN, and the discrimination may be performed only using a signal waveform in a form of a pulse signal such as a one-shot pulse or a continuous pulse.

In addition, although, in this example, an example where gain setting is performed has been described, the gain setting may be omitted as described in the subsequent embodiments.

Second Embodiment

Figure 11:
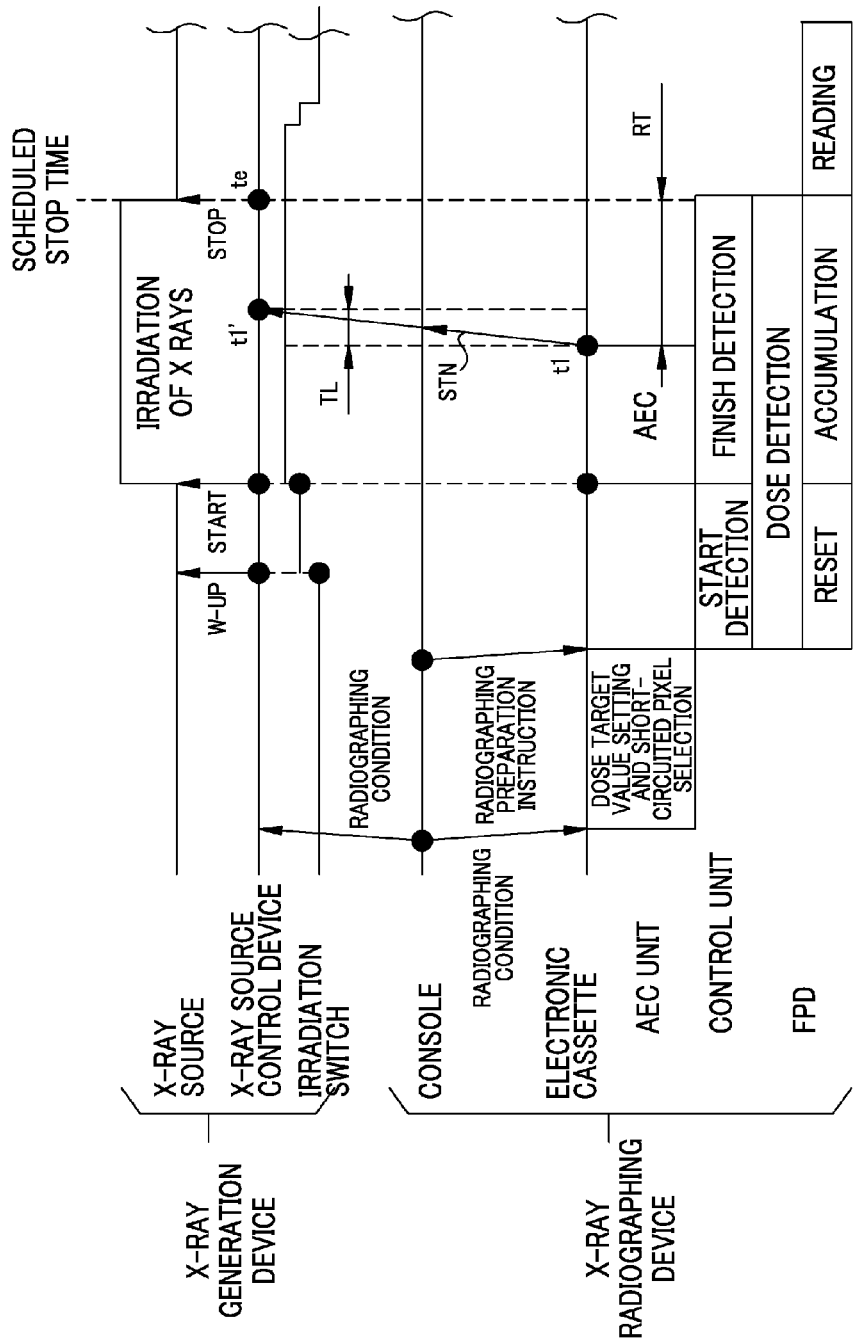
FIG. 11 is a flowchart illustrating procedures of an embodiment of stopping irradiation of X rays based on a scheduled stop time.
Figure 12:
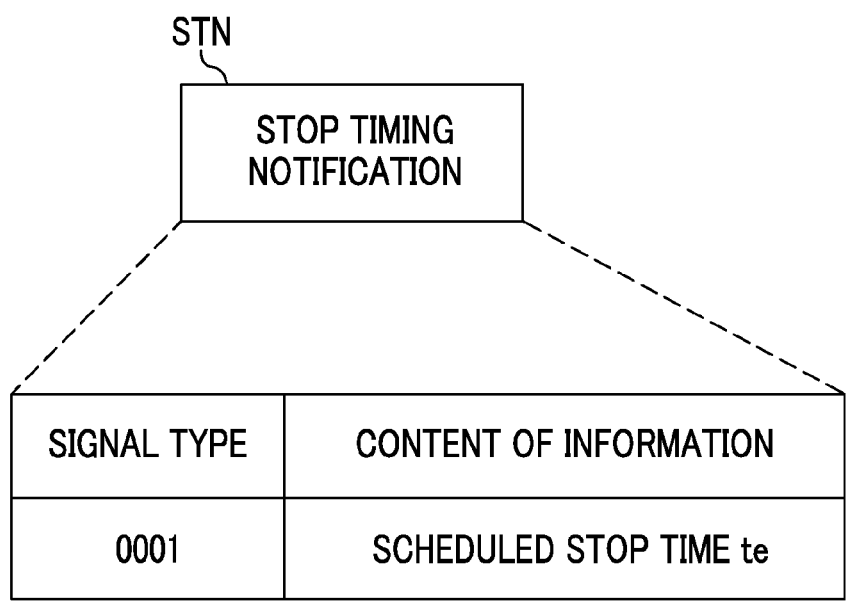
FIG. 12 is a diagram illustrating a data format of a stop timing notification including a scheduled stop time according to a second embodiment.
Figure 13:
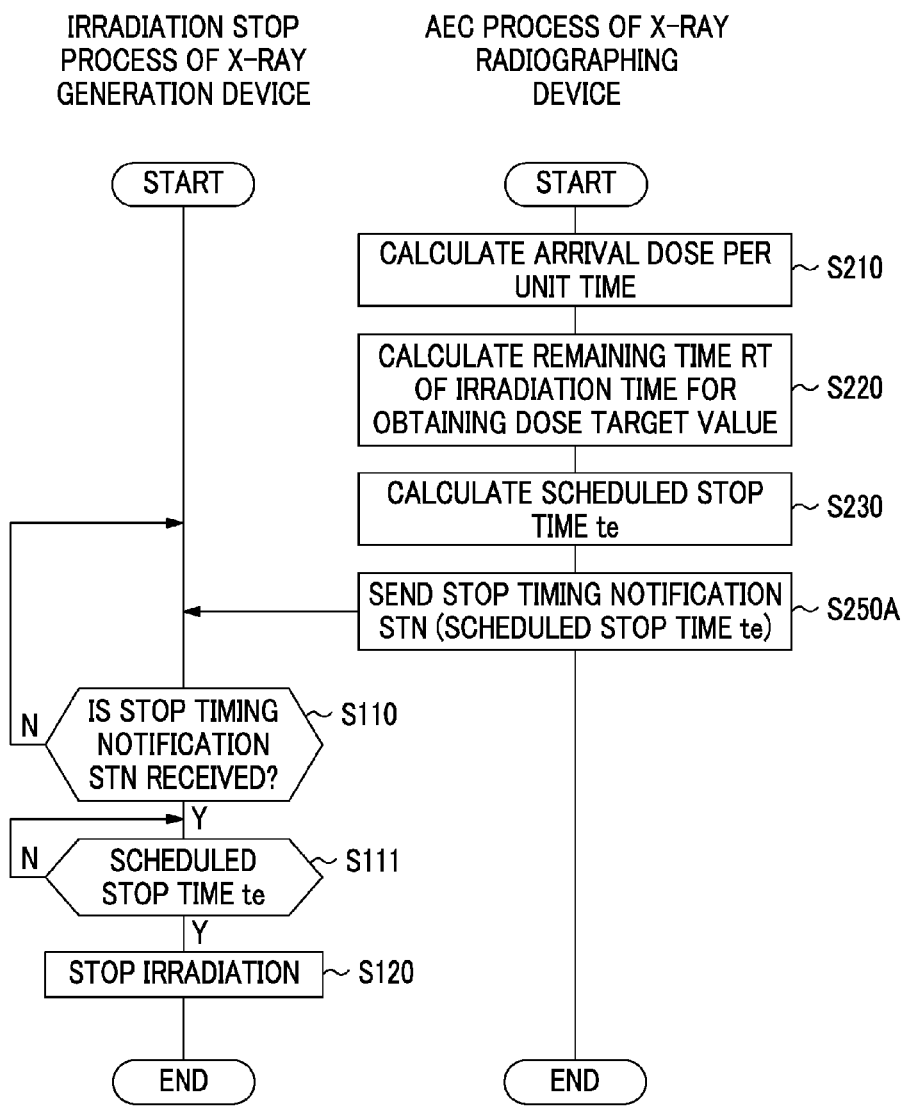
FIG. 13 is a flowchart illustrating procedures of an AEC process using a scheduled stop time according to the second embodiment.

Although, in the first embodiment, an example in which sending of the stop timing notification STN is awaited up to the time point t2 which is the predetermined time TL earlier than the scheduled stop time te after the AEC process finishes has been described, the stop timing notification STN may be sent at the time point t1 when the AEC process finishes as in the second embodiment illustrated in FIGS. 11 to 13. Description of the common parts to the first embodiment, and the description will be made mainly based on differences.

As illustrated in FIG. 11, in a case of the second embodiment, the electronic cassette 12 sends the stop timing notification STN at the time point t1 when prediction of the scheduled stop time te is completed in the AEC process. For this reason, the stop timing notification STN arrives at the X-ray source control device 16 at the time point t1' which is the predetermined time TL later than the time point t1. In a case where the time from the time point t1 to the scheduled stop time te is longer than the predetermined time TL, the X-ray source control device 16 waits for the irradiation of X rays to stop until the scheduled stop time te after receiving the stop timing notification STN. In addition, in the present embodiment, the time point t1 is used as a reference time point.

As illustrated in a data format of FIG. 12, the stop timing notification STN of this example includes information of the scheduled stop time te along with a signal type. The information of the scheduled stop time te is time point information indicated by, for example, "hour, minute, and second", and, particularly, the "second" is indicated with the millisecond unit so as to execute the AEC in radiographing during irradiation time of an extent of milliseconds.

As illustrated in FIG. 13, when the scheduled stop time te is calculated, the control unit 36 of the electronic cassette 12 generates the stop timing notification STN including the scheduled stop time te, and sends the stop timing notification STN to the X-ray source control device 16 at the time point t1 when the prediction is completed (S250A). When the stop timing notification STN is received (S110), the control unit 20 of the X-ray source control device 16 reads the scheduled stop time te from the stop timing notification STN. In addition, the control unit 20 compares the current time clocked by the clock circuit 20a with the scheduled stop time te and determines whether or not the current times reaches the scheduled stop time te (S111). Further, if the control unit 20 determines that the current time reaches the scheduled stop time te, the control unit 20 stops the irradiation of X rays (S120).

In the second embodiment, since the stop timing notification STN is sent earlier than in the first embodiment, for example, even in a case where a time lag of the predetermined time TL or more occurs in transmission of the stop timing notification STN, the arrival time t1' at the X-ray source control device 16 is considered to be earlier than the scheduled stop time te, and thus the irradiation of X rays can stop at the scheduled stop time te.

In addition, as in this example, in a case where the scheduled stop time te is included in the stop timing notification STN, time points of the respective clock circuits 36a and 20a of the electronic cassette 12 and the X-ray source control device 16 are required to match each other. For this reason, preferably, time points of both the clock circuits 36a and 20a are made to match each other. In a time point synchronization process of the clock circuits 36a and 20a, for example, when radiographing conditions are transferred from the console 13 to the electronic cassette 12 and the X-ray source control device 16, time point information and a synchronization instruction signal is transferred from the console 13. When the synchronization instruction signal is received, the electronic cassette 12 and the X-ray source control device 16 correct the clock circuits 36a and 20a based on the time point information. Thereby, time point synchronization is completed. The control unit 73 of the console 13 corresponds to a time point synchronization unit.

In addition, if a time lag of communication occurs when the synchronization instruction signal or clock information is transferred, each arrival time of the electronic cassette 12 and the X-ray source control device 16 is shifted. Particularly, whereas the electronic cassette 12 and the console 13 are connected in a wireless manner, the console 13 and the X-ray source control device 16 are connected in a wired manner, and thus there is a high probability that a difference may occur in communication time or a time lag of communication. The time lag of communication tends to be problematic in the wireless manner, and thus time point synchronization is preferably performed at timing when or a place where an electric wave becomes favorable. In addition, automatic communication may be performed so as to be executed when the system is activated every day, thereby executing the time point synchronization. Of course, an operator or a service man may manually perform the time point synchronization.

In addition, in a case where the stop timing notification STN includes the scheduled stop time te, the electronic cassette 12 receives the stop timing notification STN sent from the console 13, and the console 13 may hold the stop timing notification STN for the time being if there is time left before the scheduled stop time te, and transmit the stop timing notification STN to the X-ray source control device 16 at the timing close to the scheduled stop time te.

Figure 14:
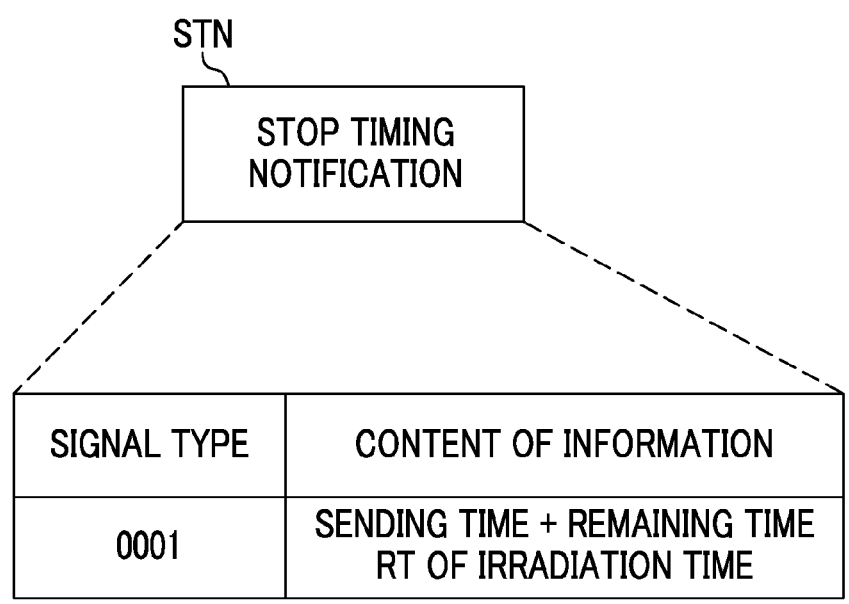
FIG. 14 is a diagram illustrating a data format of a stop timing notification including a sending time and a remaining time according to the second embodiment.
Figure 15:
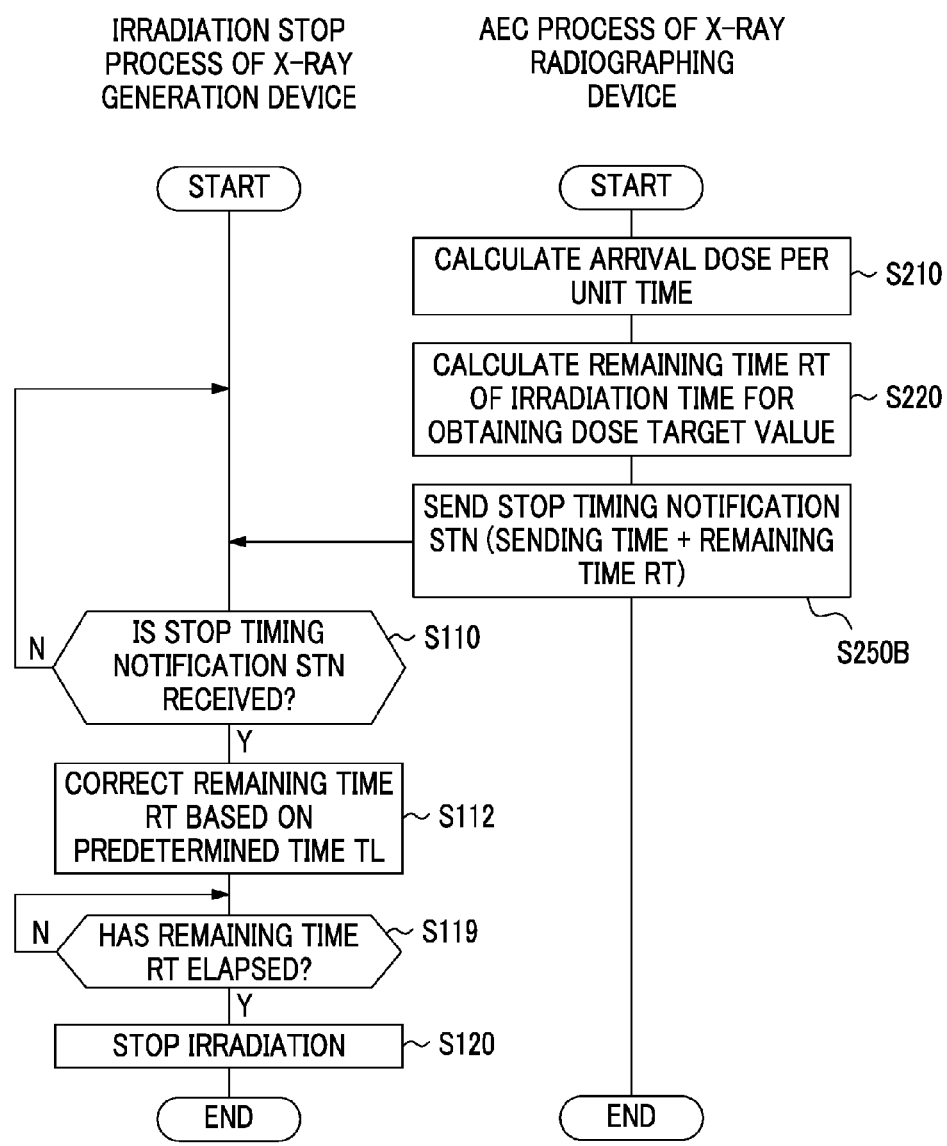
FIG. 15 is a flowchart illustrating procedures of an AEC process using the sending time and the remaining time according to the second embodiment.

In the second embodiment, various aspects of the stop timing notification STN may be considered. For example, as illustrated in FIGS. 14 and 15, as information included in the stop timing notification STN, a remaining time RT of an irradiation time required for obtaining a dose target value from the reference time point may be used instead of the scheduled stop time te. The remaining time RT is obtained in process step S220 when the scheduled stop time te is predicted is obtained as illustrated in FIGS. 10, 13 and 15.

The control unit 36 of the electronic cassette 12 calculates the remaining time RT, and then performs process step S250B without calculating the scheduled stop time te. In this example, the reference time point is, for example, a sending time (refer to the time point t1 in FIG. 11) when the stop timing notification STN is sent from the electronic cassette 12 as illustrated in FIG. 14. As illustrated in FIG. 15, the control unit 36 of the electronic cassette 12 generates the stop timing notification STN including the sending time and the remaining time RT and sends the stop timing notification STN to the X-ray source control device 16 in process step S250B.

In FIG. 15, when the stop timing notification STN is received (S110), the control unit 20 of the X-ray source control device 16 reads the sending time and the remaining time RT from the stop timing notification STN. The remaining time RT is corrected based on the predetermined time TL (S112). This is, as illustrated in FIG. 11, aimed at correcting a time lag of communication between the electronic cassette 12 and the X-ray source control device 16. The stop timing notification STN which is sent from the electronic cassette 12 at the time point t1 arrives at the X-ray source control device 16 at the time point t1' after the predetermined time TL. Since the remaining time RT is obtained using the time point t1 as the reference time point, the control unit 20 performs correction for subtracting the predetermined time TL from the remaining time RT. In addition, the control unit 20 sets the remaining time RT in the timer 23 and monitors elapsing of the remaining time RT (S119). A time point when the remaining time RT has elapsed becomes the scheduled stop time te, and thus the control unit 20 stops the irradiation of X rays at the time point when the remaining time RT has elapsed.

In this example, only the X-ray source control device 16 corrects the remaining time RT; however, the electronic cassette 12 may correct the remaining time RT. For example, the remaining time RT is calculated in the step where the scheduled stop time te is predicted, and, there is a time difference between the calculation time point and the sending time although slight. Of course, although the difference is slight as compared with communication time or a time lag of communication, this correction may be performed in a case where high accuracy is desired to be obtained.

Figure 16:
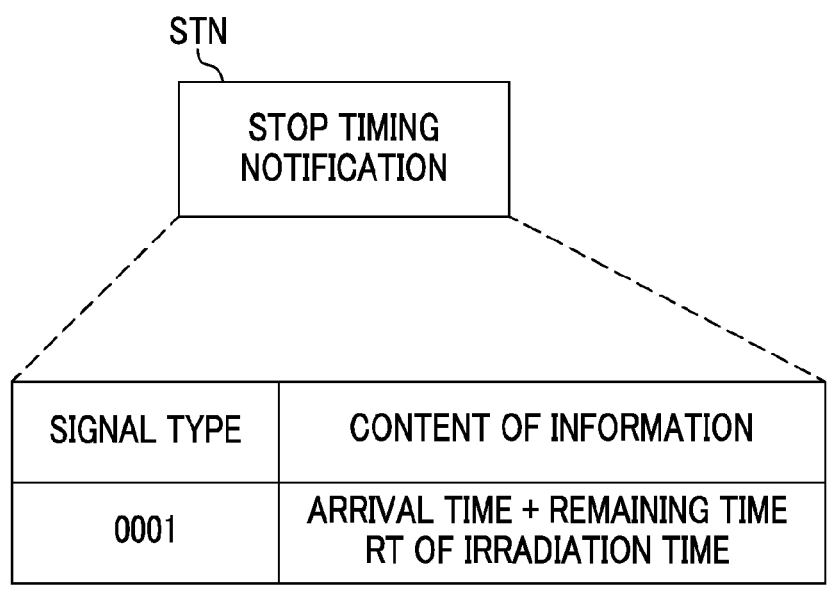
FIG. 16 is a diagram illustrating a data format of a stop timing notification including an arrival time and a remaining time according to the second embodiment.
Figure 17:
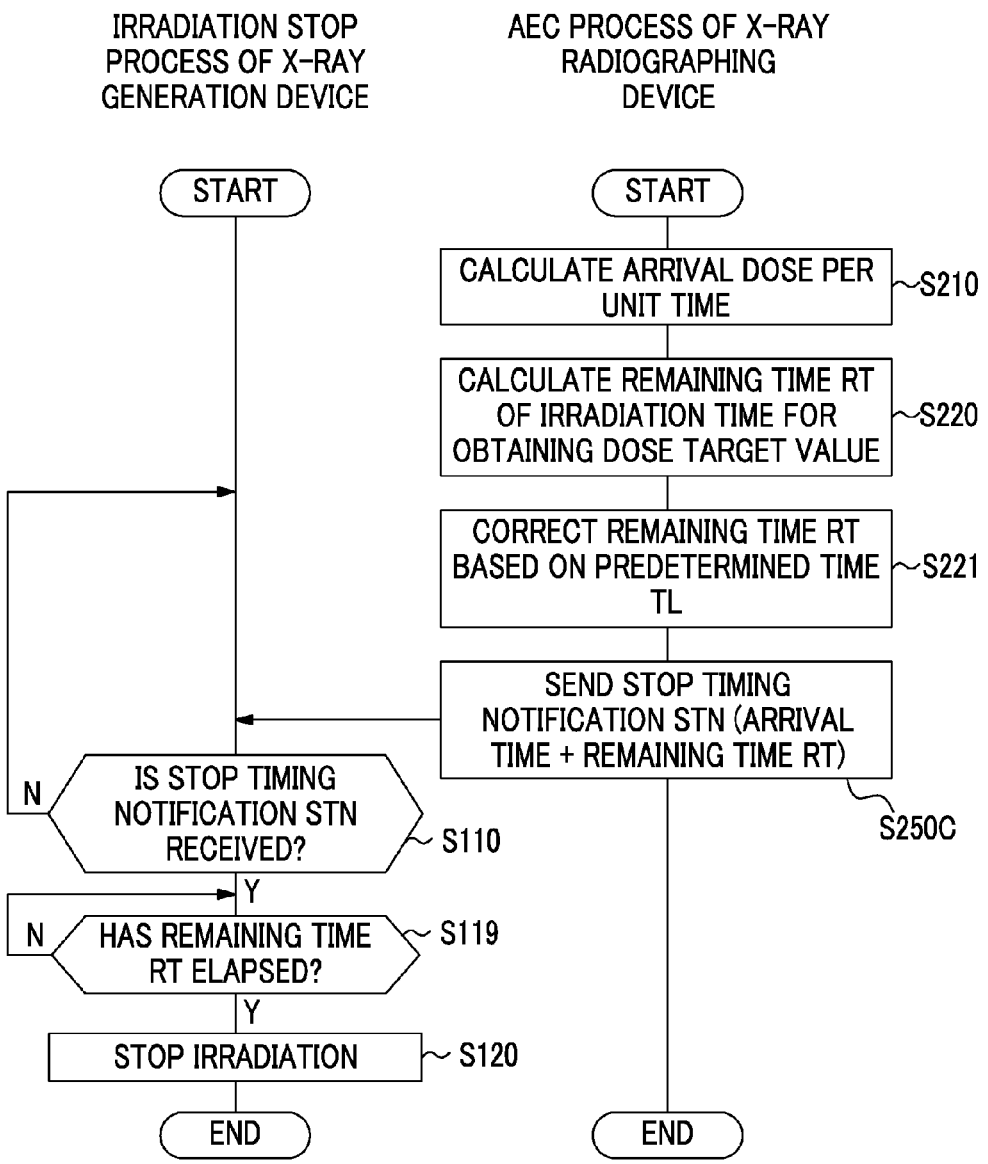
FIG. 17 is a flowchart illustrating procedures of an AEC process using the arrival time and the remaining time according to the second embodiment.

In addition, as illustrated in FIGS. 16 and 17, an arrival time when the stop timing notification STN arrives at the X-ray source control device 16 may be included in the stop timing notification STN instead of the sending time. In this case, as illustrated in FIG. 17, the remaining time RT is corrected (S221). The remaining time RT uses an arrival time as a reference time point, and thus the control unit 36 of the evaluation portion 21 performs correction for subtracting the predetermined time TL from the calculated remaining time RT in process step S221. In addition, the control unit 36 obtains an arrival time by adding the predetermined time TL to the sending time. The control unit 36 includes the arrival time and the remaining time RT in the stop timing notification STN which is sent (S250C).

In the X-ray source control device 16, the control unit 20 reads the arrival time and the remaining time RT from the received stop timing notification STN. When a reference time point is confirmed to be the arrival time, the control unit 20 sets the remaining time RT in the timer 37 and monitors elapsing of the remaining time RT. As illustrated in FIG. 11, the control unit 20 stops irradiation at a time point when the remaining time RT has elapsed.

Figure 18:
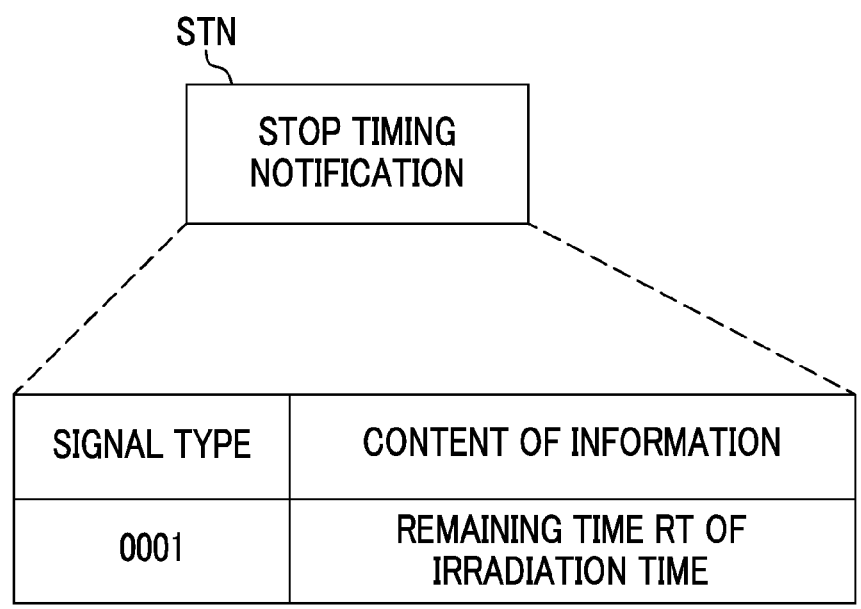
FIG. 18 is a diagram illustrating a data format of a stop timing notification including a remaining time according to the second embodiment.

In addition, as in the stop timing notification STN illustrated in FIG. 18, the reference time point is not included, and only the remaining time RT may be included. In this case, which one of the electronic cassette 12 and the X-ray source control device 16 corrects the predetermined time TL is determined. In this way, even if the reference time point is not included, the remaining time RT may be appropriately corrected based on the predetermined time TL according to determined procedures in advance.

In the second embodiment, the data formats described with reference to FIGS. 12, 14, 16 and 18 and the process procedures may be combined with the first embodiment. The first embodiment is an aspect in which, as illustrated in FIG. 10, the stop timing notification STN is sent from the electronic cassette 12 before the predetermined time TL of the scheduled stop time te so as to arrive at the X-ray source control device 16 exactly at the scheduled stop time te.

As described above, the predetermined time TL is an average value of communication time or a time lag of communication, and has an error with real communication time or time lag of communication. There are cases where the real communication time or time lag of communication is longer than or shorter than the predetermined time TL. In a case where the real communication time or time lag of communication is longer than the predetermined time TL, since an arrival time of the stop timing notification STN has already past the scheduled stop time te, correction cannot be performed. However, in a case where the real communication time or time lag of communication is shorter than the predetermined time TL, an arrival time is earlier than the scheduled stop time te. In a case where the current time does not reach the scheduled stop time te when the stop timing notification STN is received, the control unit 20 of the X-ray source control device 16 does not immediately stop the irradiation of X rays but waits for the stop timing to arrive and stops the irradiation of X rays. In this way, even if there is an error between the predetermined time TL and the real communication time, irradiation can stop exactly at the stop timing.

In addition, the reference time point included in the stop timing notification STN may use time points other than the sending time in the electronic cassette 12 or the arrival time in the X-ray source control device 16, or may use a sending time in the console 13. In that case, when the stop timing notification STN is received from the electronic cassette 12, the console 13 corrects the remaining time RT so as to be suitable for the sending time in the console 13, and transmits the stop timing notification STN to the X-ray source control device 16.

The various aspects of the stop timing notification STN described in the second embodiment may be applied to almost all the subsequent embodiments from the third embodiment.

Third Embodiment

Figure 19:
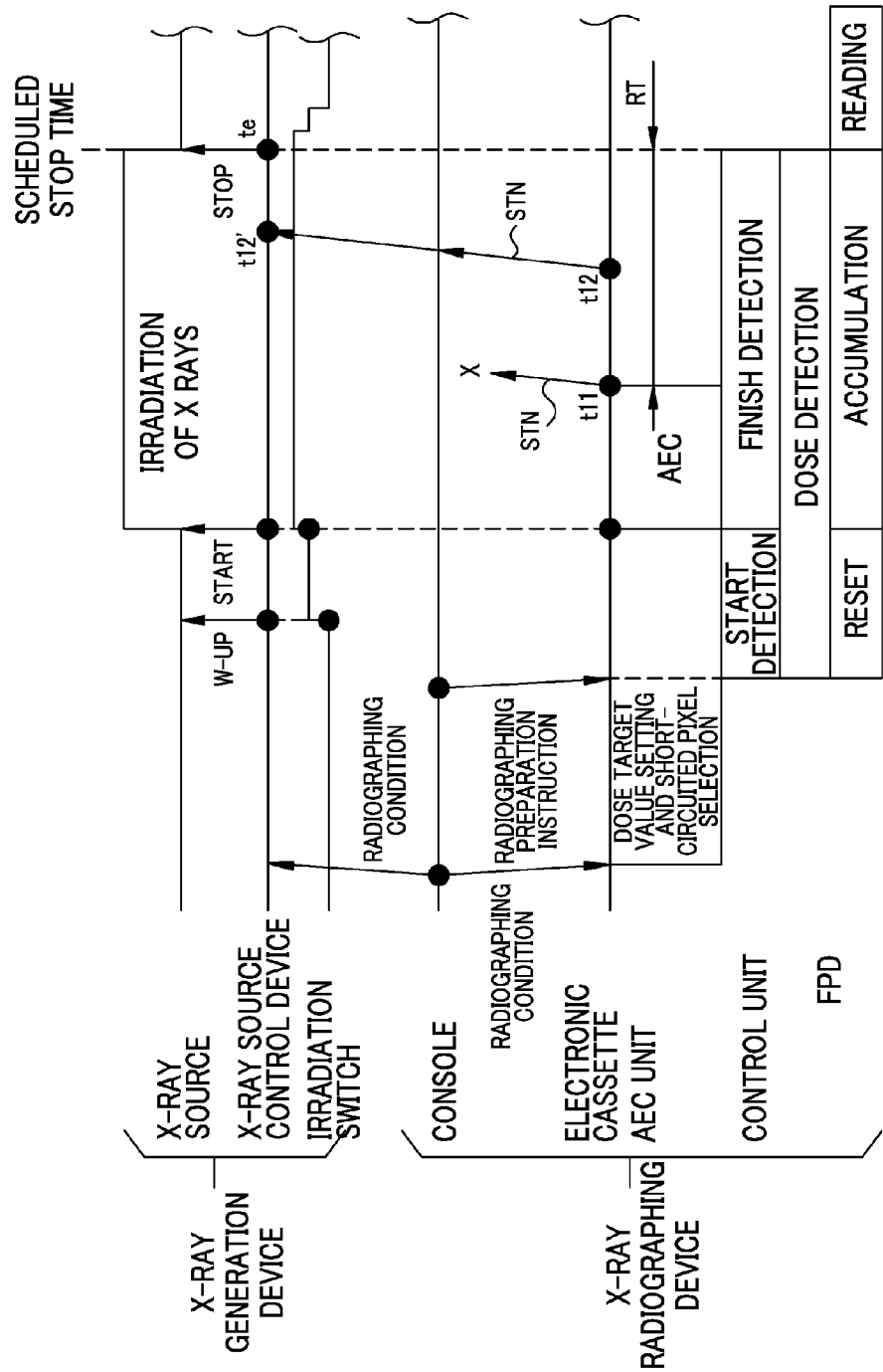
FIG. 19 is a timing chart illustrating procedures of an AEC process according to a third embodiment.

The third embodiment illustrated in FIG. 19 is an example where the stop timing notification STN is retransferred after irradiation of X rays starts until the irradiation stops, that is, until a cumulative dose reaches a dose target value. The example illustrated in FIG. 19 is an example in which transmission is retried in a case where the stop timing notification STN sent by the electronic cassette 12 does not arrive at the X-ray source control device 16 due to instantaneous interruption of the communication path or time-out when a time lag of communication is long.

In FIG. 19, the electronic cassette 12 performs the AEC process, and sends the stop timing notification STN at the time point t11. At the first transmission timing, a case where the stop timing notification STN does not arrive at the X-ray source control device 16 due to instantaneous interruption of the communication path or the like is illustrated. The electronic cassette 12 retries transmission of the stop timing notification STN at a predetermined interval in preparation for this case of communication failure. The stop timing notification STN is sent at the time point t12 which is the timing when the communication path is recovered and thus arrives at the X-ray source control device 16.

As such, a plurality of transmissions of the stop timing notification STN are repeatedly performed, and thereby communication failure such as instantaneous interruption of a communication path can be handled. In a case of a wireless manner, since an electric state is unstable and thus communication failure frequently occurs, the present invention is particularly useful.

In the example of FIG. 19, aspects of the stop timing notification STN may be an aspect in which the scheduled stop time te illustrated in FIG. 12 may be included, and an aspect in which the remaining time RT illustrated in FIGS. 14, 16 and 18 is included.

Here, a process is different depending on whether the scheduled stop time te is included or the remaining time RT is included. In a case of including the scheduled stop time te, the scheduled stop time te does not vary even if the sending time varies to the time point t11 and the time point t12, and thus the stop timing notification STN of the same content is transferred at any one of the time point t11 and the time point t12. On the other hand, the remaining time RT is defined as time left from a reference time point, and thus remaining time RT using each of the time point t11 and the time point t12 as a reference time point is changed. For this reason, in a case where transmission of the stop timing notification STN which is sent at the time point t11 is retried at the time point t12, the remaining time RT is corrected according to a time difference between the time point t11 and the time point t12. Specifically, in a case where the remaining time RT using the time point t11 as a reference time point is transferred at the time point t12, correction for subtracting the time difference between the time point t11 and the time point t12 from the remaining time RT is performed. In addition, in a case where a transmission time or an arrival time is included along with the remaining time RT, the transmission time or the arrival time is also updated according thereto. In addition, in the present embodiment, the time point t12 is used as a reference time point.

In a case of a plurality of transmissions of the stop timing notification STN are repeatedly performed at a predetermined time interval as in this example, there are cases where the X-ray source control device 16 receives a plurality of stop timing notifications STN. In a case where the scheduled stop time to is included in the stop timing notification STN, the same content is given, and thus there is no problem; however, in a case of including the remaining time RT, a value of the remaining time RT is changed in a plurality of stop timing notifications STN. In this case, since the stop timing notification STN of which the remaining time RT is the minimum is regarded as being the latest out of a plurality of stop timing notifications STN, the X-ray source control device 16 may select the stop timing notification STN of which the remaining time RT is the minimum and may stop irradiation according to the remaining time RT.

When the stop timing notification STN is received, the X-ray source control device 16 may transmit a reception acknowledgement signal to the electronic cassette 12. In this way, since the electronic cassette 12 receiving the reception acknowledgement signal stops the retry, a plurality of stop timing notifications STN are prevented from being transferred to the X-ray source control device 16.

Fourth Embodiment

Figure 20:
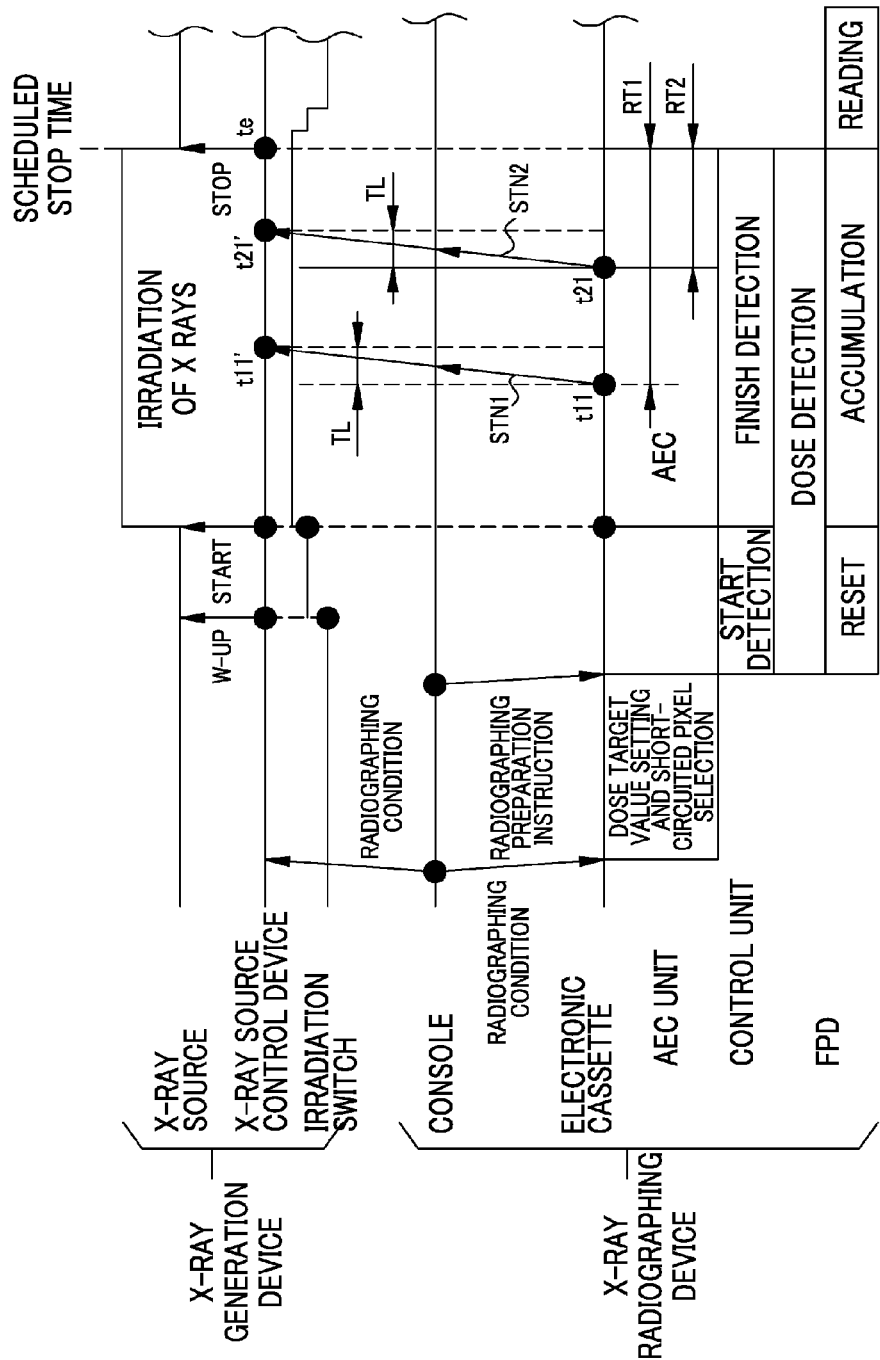
FIG. 20 is a timing chart illustrating procedures of the AEC process according to a fourth embodiment.
Figure 21:
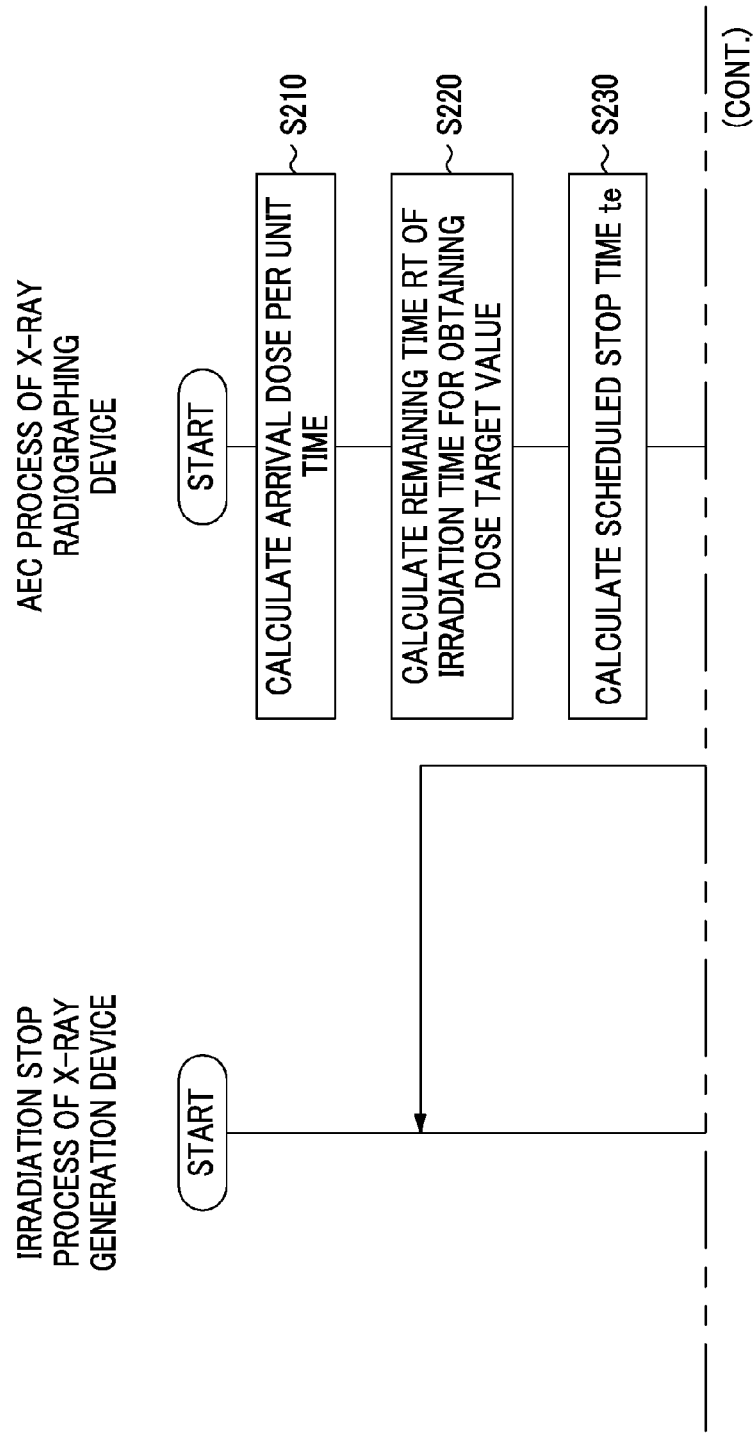
FIG. 21 is a flowchart illustrating procedures of an AEC process according to the fourth embodiment.

The fourth embodiment illustrated in FIGS. 20 and 21 is the same as the third embodiment in that a plurality of stop timing notifications STN are repeatedly sent during irradiation. A difference is that a stop timing is predicted again each time the stop timing notification STN is sent in the fourth embodiment. The later the time point when prediction is performed, the larger the cumulative dose, and thus prediction accuracy can be improved.

In FIG. 20, the electronic cassette 12 performs the AEC process until a cumulative dose reaches a dose target value, and repeatedly predicts a stop timing during that time. At the time point t11, the first prediction of a stop timing is performed, and the first stop timing notification STN1 is sent. In addition, at the time point t21 after a predetermined time has elapsed, the second prediction is performed, and the second stop timing notification STN2 is sent. The stop timing notifications STN1 and STN2 arrive at the X-ray source control device 16 at time points t11' and t21', respectively. In addition, in the present embodiment, the time points t11 and t21 are used as reference time points.

As illustrated in FIG. 21, the stop timing notifications STN1 and STN2 may include, for example, a scheduled stop time te. The electronic cassette 12 executes process steps S210 to S230 and S250A illustrated in FIG. 13, and sends the first stop timing notification STN1. In addition, after a predetermined time has elapsed, the scheduled stop time te is calculated again based on a cumulative dose at that time point, and performs the second prediction (S260). The electronic cassette 12 executes the same process step S270 as process step S250A, and sends the stop timing notification STN2. These processes are repeatedly performed until a cumulative dose reaches the dose target value (S280).

On the other hand, the X-ray source control device 16 performs a plurality of receptions of the stop timing notification STN (S110A). Both of the stop timing notifications STN1 and STN2 include the scheduled stop time te; however, the scheduled stop time te included in the stop timing notification STN2 is calculated again, and thus has high prediction accuracy. The X-ray source control device 16 selects the latest scheduled stop time te based on the receiving time (S1102A), and monitors that the selected scheduled stop time te arrives (S111). When the scheduled stop time te arrives, irradiation stops (S120). According to this example, the stop timing is repeatedly predicted again, and thus high accuracy AEC can be performed. Thereby, an excessive dose is reduced, and improvement in image quality of an X-ray image and reduction in an unnecessary exposure dose of the subject H can be expected.

Although, in this example, the latest stop timing notification STN is determined based on a receiving time in the X-ray source control device 16, a sending time or an arrival time may be set in the stop timing notifications STN1 and STN2, respectively, in the electronic cassette 12, in addition to the scheduled stop time te. In this way, the X-ray source control device 16 can determine the latest stop timing notification STN based on the sending time or the arrival time included in the stop timing notification STN.

Figure 22:
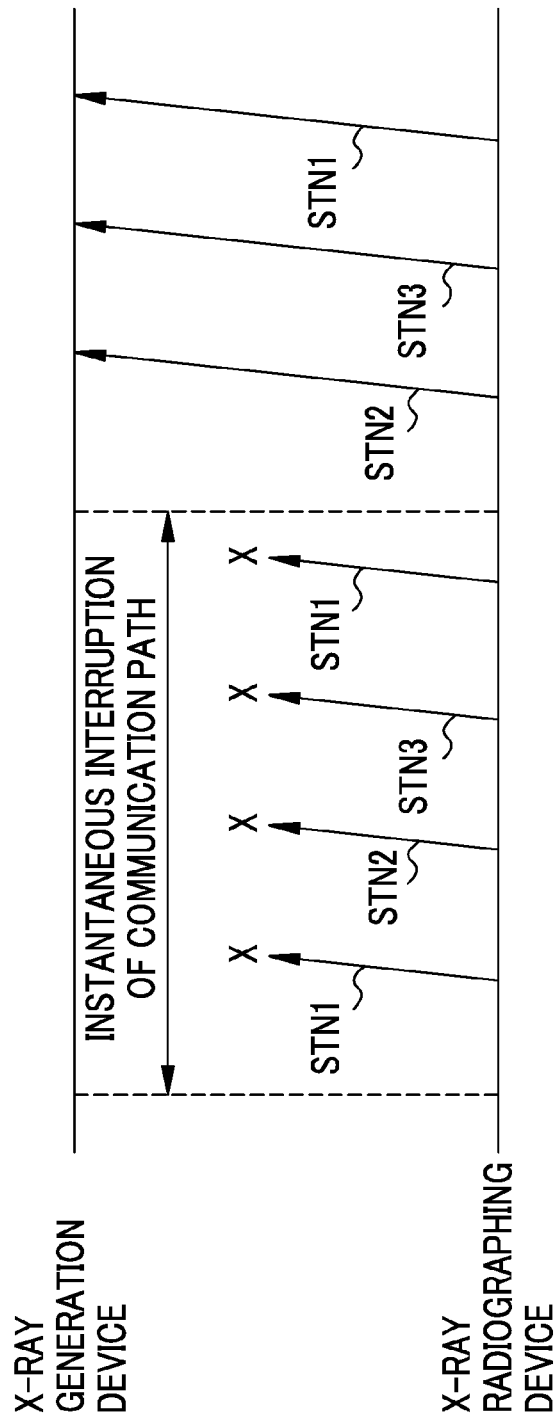
FIG. 22 is a timing chart illustrating a state where an order of reception timings of a plurality of stop timing notifications is wrong due to recovery of communication failure in the fourth embodiment.

As illustrated in FIG. 22, in a case where a plurality of stop timing notifications STN are transferred, when instantaneous interruption of a communication path occurs, there are cases where an order of reception timings of a plurality of stop timing notifications STN is wrong. The example of FIG. 22 illustrates a case where the stop timing notifications STN1, STN2 and STN3 are transferred in this order, none of the three stop timing notifications are transferred at the timings due to instantaneous interruption of the communication path, and then transmission of the three stop timing notifications STN1, STN2 and STN3 are retried. A stop timing notification of which transmission is first retried is the stop timing notification STN1; however, the instantaneous interruption continues at this time, and thus the stop timing notification STN1 is not transferred. Since the communication failure is recovered at the timings when transmission of the subsequent stop timing notifications STN2 and STN3 is retried, the transmission of the stop timing notifications STN2 and STN3 is successful. Transmission of the stop timing notification STN1 is successful thirdly, and thus an order thereof to be received is later than the stop timing notifications STN2 and STN3.

In this case, if determination is performed at the sending time, the latest stop timing notification is the stop timing notification STN3, but, if determination is performed at the receiving time, the latest stop timing notification is determined as being the stop timing notification STN1. In this case, if a sending time is set in the stop timing notification STN in the electronic cassette 12, the X-ray source control device 16 can correctly determine the latest notification even if the reception order is changed.

Figure 23:
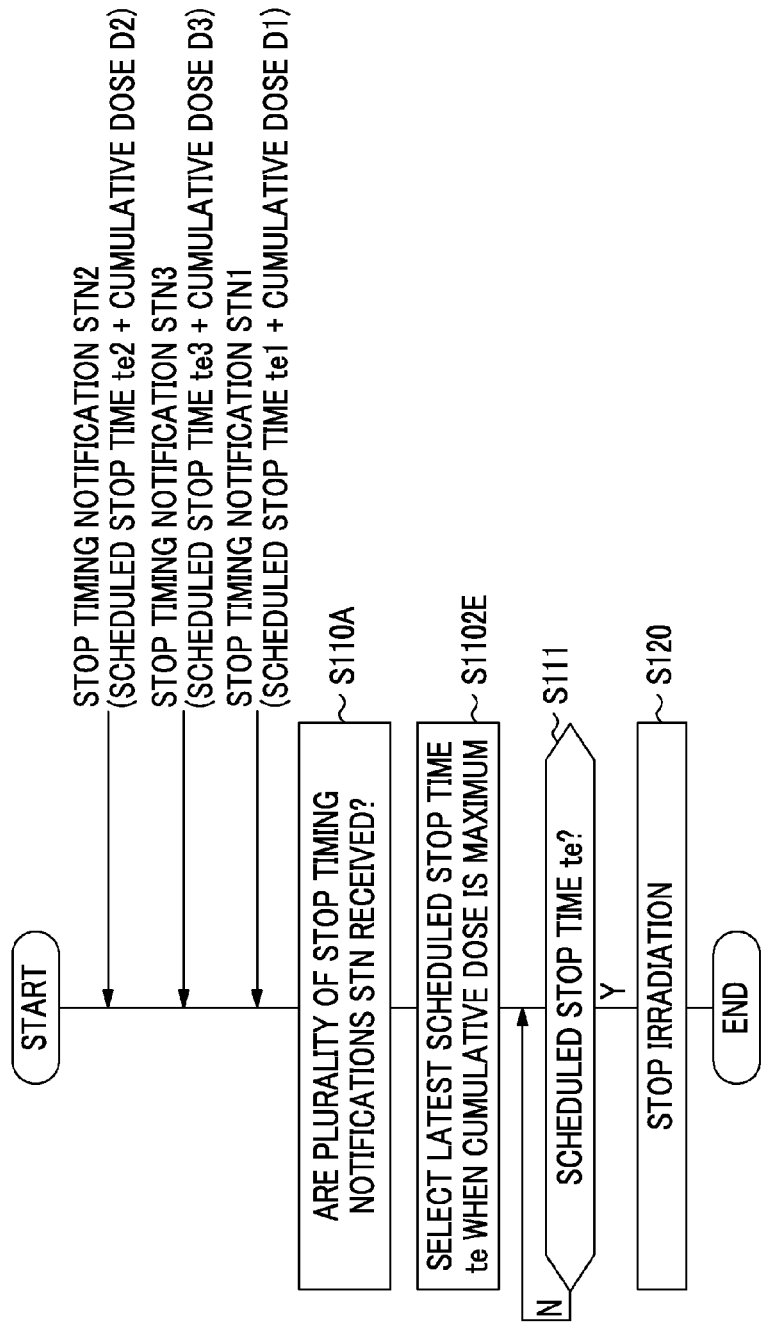
FIG. 23 is a flowchart illustrating procedures of the AEC process where information of a cumulative dose is included in the stop timing notification in the fourth embodiment.

As illustrated in FIG. 23, cumulative doses D1, D2 and D3 respectively may be set in the stop timing notifications STN1, STN2 and STN3 in addition to the respective scheduled stop times te1, te2 and te3. The cumulative doses D1, D2 and D3 are used to predict the scheduled stop times te1, te2 and te3. Since the cumulative doses D1, D2 and D3 increase with the passage of time, the later, the greater the value thereof. For this reason, the control unit 20 of the X-ray source control device 16 determines that the stop timing notification STN3 of which a cumulative dose is the maximum is the latest notification and employs the scheduled stop time te3 thereof in process step S1102E.

Figure 24:
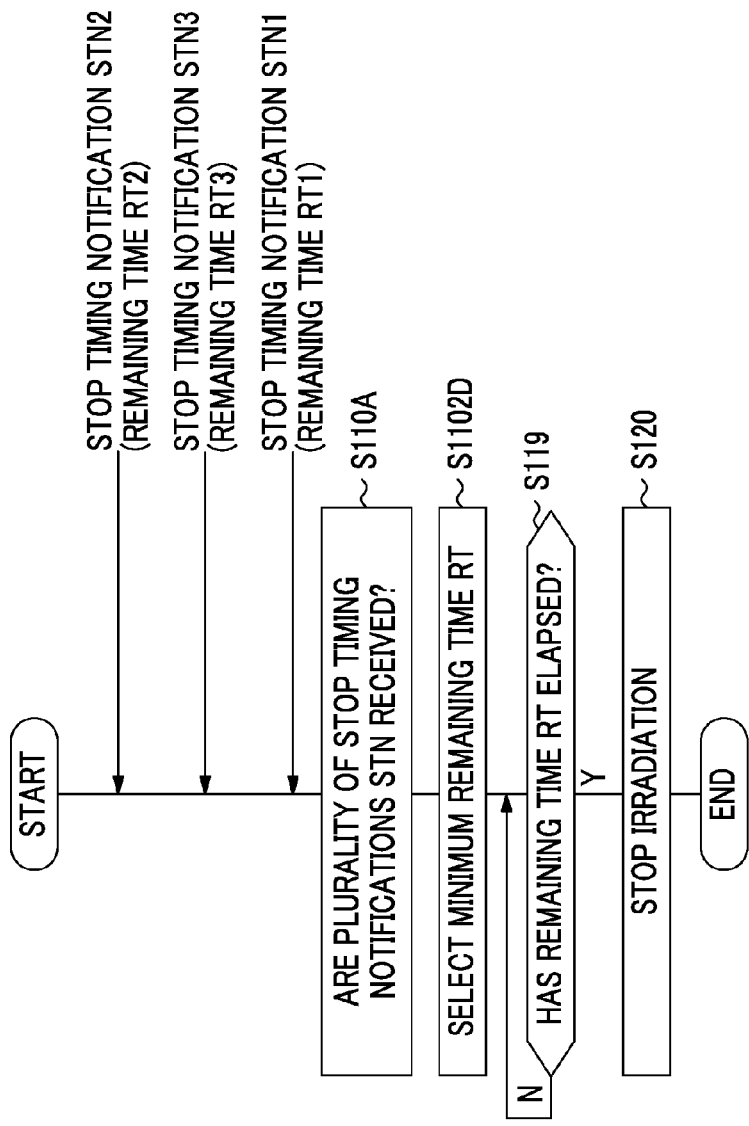
FIG. 24 is a flowchart illustrating procedures of the AEC process where a remaining time is included in the stop timing notification in the fourth embodiment.

In addition, although, in this example, an example where the scheduled stop time to is set in the stop timing notification STN has been described, the remaining time RT may be set as illustrated in FIG. 24. In a case of the remaining time RT, as illustrated in process step S1102D, the latest stop timing notification STN can be determined using the remaining time RT itself. This is because, the later the remaining time RT, the smaller the value thereof. Of course, in order to further increase accuracy, a sending time, an arrival time, a cumulative dose, and the like may be set.

Fifth Embodiment

Figure 25:
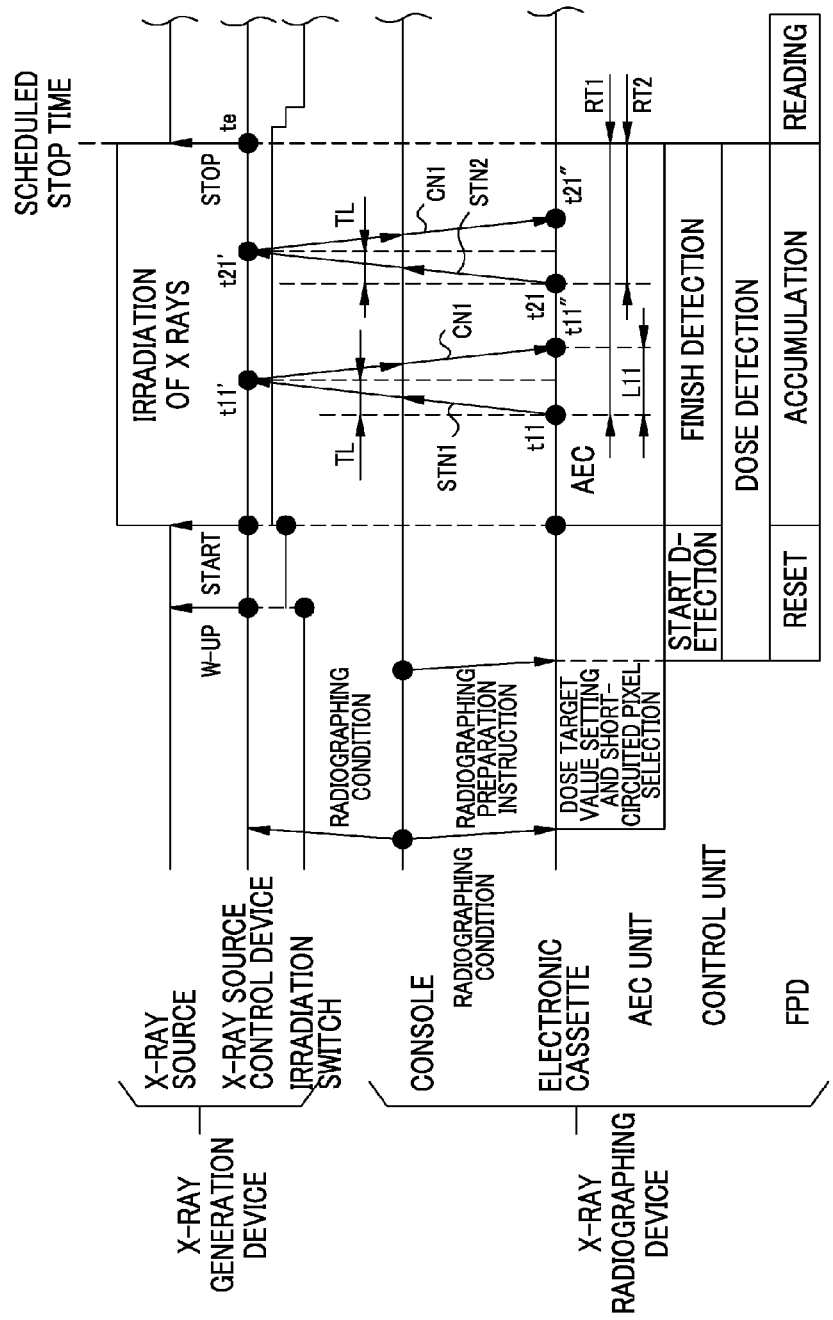
FIG. 25 is a timing chart illustrating procedures of an AEC process according to a fifth embodiment.
Figure 26:
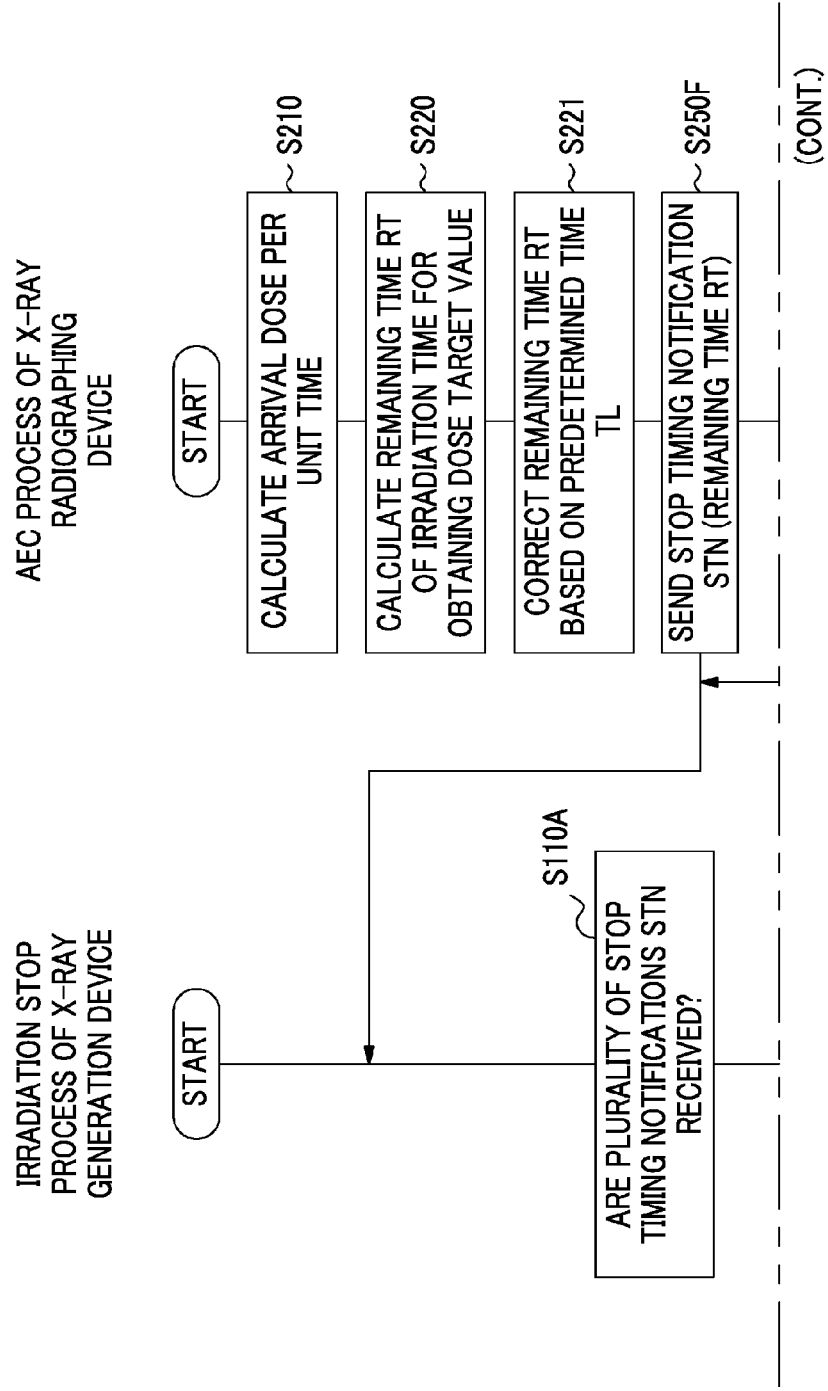
FIG. 26 is a flowchart illustrating procedures of the AEC process according to the fifth embodiment.

The fifth embodiment illustrated in FIGS. 25 and 26 is an example in which the stop timing notification STN is transferred from the electronic cassette 12 to the X-ray source control device 16, and the X-ray source control device 16 returns a reception acknowledgement signal CN to the electronic cassette 12 when the stop timing notification STN is received. In addition, in the fifth embodiment, the electronic cassette 12 corrects a predetermined time TL of the stop timing notification STN2 which is transferred next based on the time L11 from the sending time t11 of the first stop timing notification STN1 to the receiving time t11' of the reception acknowledgement signal CN1 which is a response thereto. In addition, in the present embodiment, the time points t11 and t21 are used as reference time points.

In other words, the time from the sending of the stop timing notification STN to the reception of the reception acknowledgement signal CN is measured, real communication time or time lag of communication is actually measured in the present communication path, and the preset predetermined time TL is corrected. This example may not be useful in a case where content set in the stop timing notification STN is the scheduled stop time te, and is useful in a case where the content is the remaining time RT. This is because, in a case of the remaining time RT, correction based on the predetermined time TL is necessary as described in the second embodiment illustrated in FIGS. 14 to 17.

As illustrated in FIG. 26, the electronic cassette 12 executes process steps S210 to S250F and sends the stop timing notification STN in which the remaining time RT is set. The X-ray source control device 16 receives the stop timing notification STN (S110A) and sends the reception acknowledgement signal CN to the electronic cassette 12 for each reception. The electronic cassette 12 performs prediction again by re-calculating the remaining time RT based on the time L11 (refer to FIG. 25) from the sending time of the stop timing notification STN to the receiving time of the reception acknowledgement signal CN (S260A). In the re-calculation, the predetermined time TL is corrected based on the time L11 in process step S221. In addition, the re-calculated remaining time RT is set in the stop timing notification STN which is transferred to the X-ray source control device 16. The X-ray source control device 16 selects the latest remaining time RT (S1102A), and performs irradiation stop. Thereby, the remaining time RT is not only predicted again but the predetermined time TL is also corrected based on an actually measured time lag of communication, and thus a stop timing can be predicated with higher accuracy.

In addition, although, in this example, a time lag of communication is actually measured using the stop timing notification STN and the reception acknowledgement signal CN, a time lag of communication may be actually measured by transmitting and receiving a test signal without using the stop timing notification STN and the reception acknowledgement signal CN.

Sixth Embodiment

Figure 27:
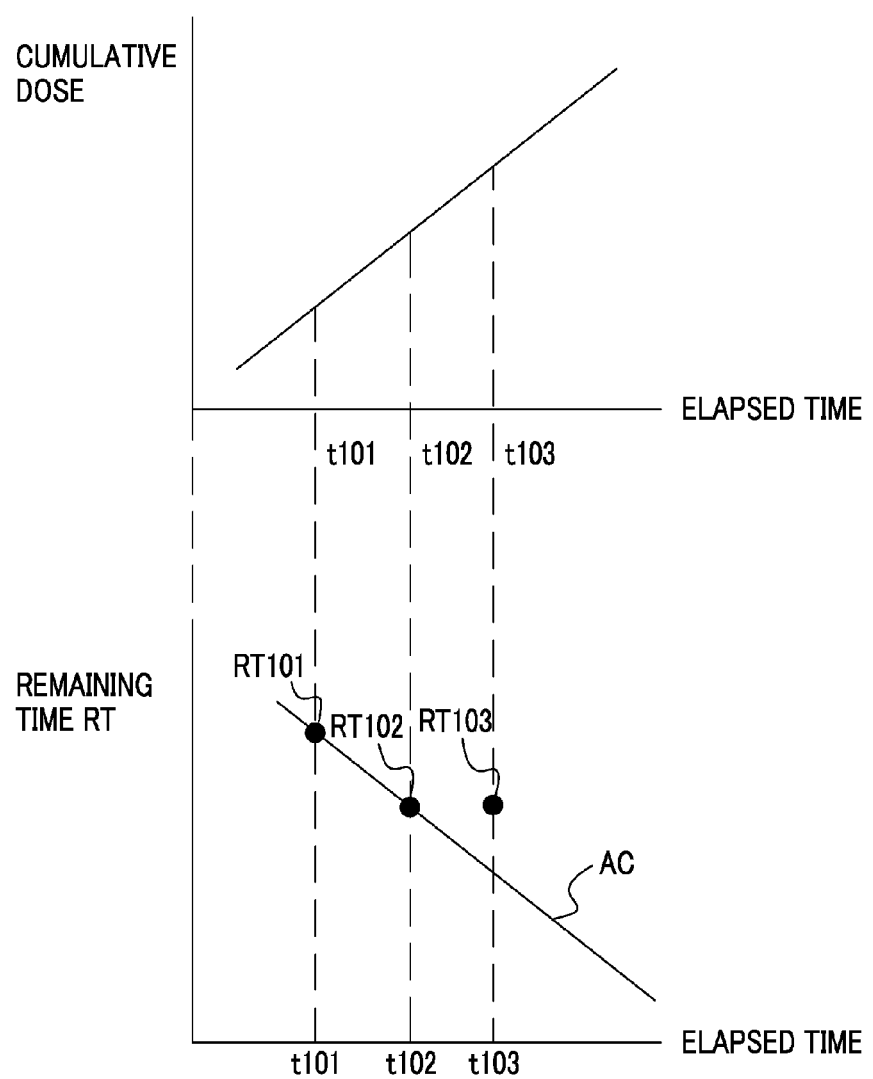
FIG. 27 is a graph illustrating a cumulative dose and an elapsed state of a remaining time in a sixth embodiment.
Figure 28:
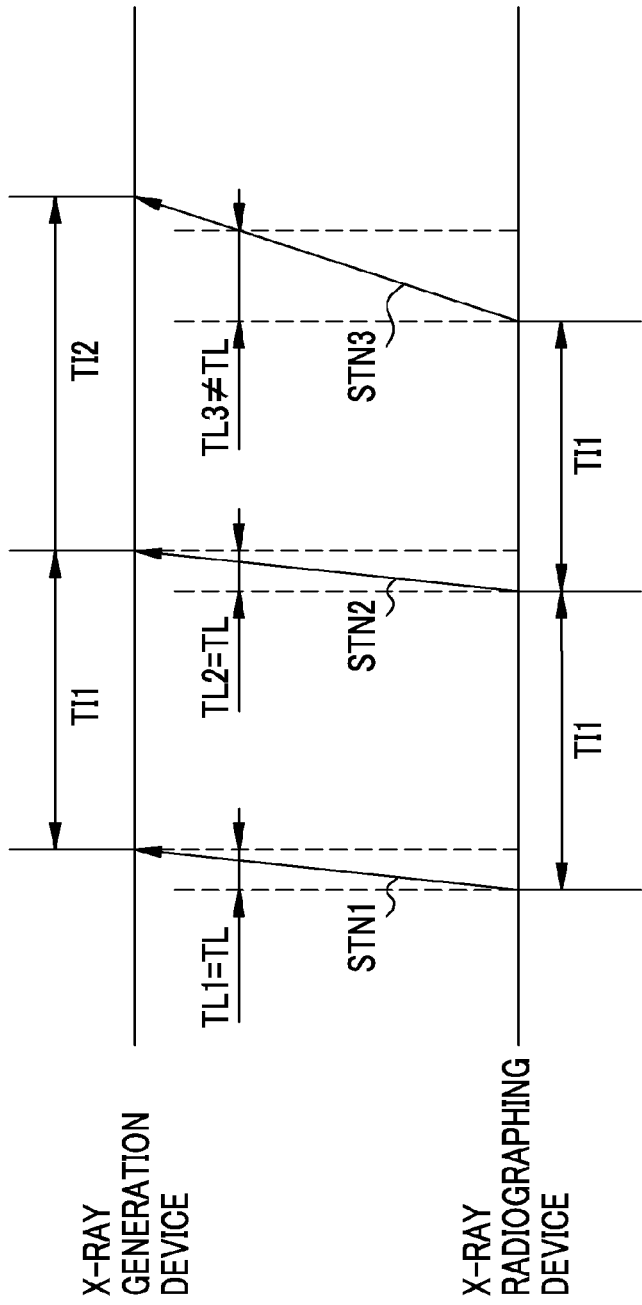
FIG. 28 is a timing chart illustrating procedures of the AEC process according to the sixth embodiment.

As a handling method in a case where a real time lag of communication and the predetermined time TL are deviated from each other, there is a method illustrated in FIGS. 27 and 28. This example corresponds to a method of handling a case where only the remaining time RT is set in the stop timing notification STN. Since the intensity of X rays applied from the X-ray source 15 becomes stable after a while from the start of irradiation, as illustrated in FIG. 27, a cumulative dose increases with a constant slope to an extent, and thereby the remaining time RT included in the stop timing notification STN which is repeatedly transferred decreases with a constant slope. The control unit 20 of the X-ray source control device 16 obtains an approximate curve AC which is linearly approximated, based on the remaining times RT101, RT102 and RT103 of a plurality of stop timing notifications STN received at the time points t101, t102 and t103.

When the approximate curve AC is obtained, it can be seen that the remaining time RT103 indicates an abnormal value among the remaining times RT101, RT102 and RT103. In relation to the remaining time RT103, a greater value thereof than the approximate curve AC means that the remaining time RT103 arrives late due to a time lag of communication although it originally arrives at the timing earlier than the time point t103. The control unit 20 of the X-ray source control device 16 determines the remaining time RT103 as having an abnormal value based on the approximate curve AC, excludes the remaining time RT103 from selection targets so as to select the latest remaining time RT102 of the remainder, and stops the irradiation of X rays. Thereby, even in a case where only the remaining time RT is set in the source electrode ST, high accuracy AEC can be performed even without using the reception acknowledgement signal CN.

Although, in the above description, an abnormal value in which a time lag of communication is great is determined using the linear approximation of the remaining time RT from a plurality of stop timing notifications STN received by the X-ray source control device 16, an abnormal value in which a time lag of communication is great may be determined based on a reception interval of a plurality of stop timing notifications STN as illustrated in FIG. 28. When the stop timing notification STN is repeatedly sent from the electronic cassette 12 at a predetermined time interval TI1, if a time lag of communication is an average value, a reception interval in the X-ray source control device 16 is the same as the time interval TI1 For this reason, when the reception interval of the stop timing notification STN varies, the stop timing notification STN of which the communication interval varies can be determined as having an abnormal value in which a time lag of communication is great.

In the example of FIG. 28, the reception interval TI2 between the stop timing notification STN2 and the stop timing notification STN3 is larger than TI1, and thus can be determined as having an abnormal value in which the real time lag TL3 of communication is greater than the predetermined time TL. In a case where only a remaining time is set in the stop timing notification STN, an abnormal value can be excluded as in this example, and thus constant prediction accuracy can be secured. Thereby, constant image quality of an X-ray image can be secured, and an unnecessary exposure of a subject can also be reduced.

Seventh Embodiment

Although, in the above-described embodiment, an example in which a value taking a time lag of communication into consideration is used for the predetermined time TL has been described, the seventh embodiment corresponds to a method of handling a case where an excessive dose exceeding a dose target value occurs due to factors other than the time lag of communication.

Figure 29:
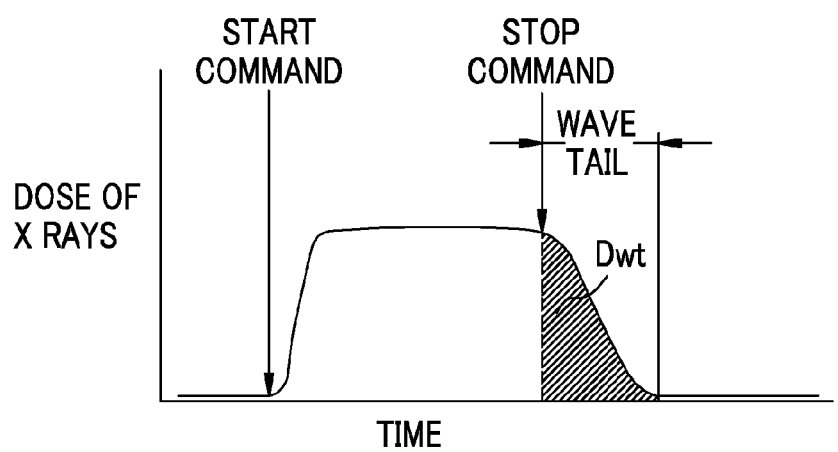
FIG. 29 is a graph illustrating a transition of a dose at one irradiation of X rays in a seventh embodiment.

As illustrated in FIG. 29, a dose of X rays gradually rises when the X-ray source 15 receives a start command, increases to a peak corresponding to a tube current, maintains an almost steady state around the peak until a stop command is received, and gradually falls when the stop command is received. As such, a curve indicating a dose variation of X rays applied in one radiographing is almost in a trapezoidal shape. In addition, the time after the stop command is received until a dose of X rays becomes completely zero, that is, a wave tail of the dose of X rays can be shortened if, for example, a high-priced X-ray source such as a triode or a tetrode is used, but is lengthened if a general X-ray source such as a diode is used. In addition, the wave tail of the dose of X rays varies depending on a tube voltage or a tube current, and, for example, the smaller the tube current, or the higher the tube voltage, the longer the wave tail.

For this reason, an irradiation amount of X rays which is practically applied varies depending on the length of the wave tail of the dose of X rays. Due to the variation in an irradiation amount, a scheduled stop time te calculated by the AEC unit 32 is deviated from a time point when a dose target value is practically obtained, and thus an excessive dose is considered to occur. In order to solve this problem, in the present embodiment, an average value of time after the X-ray source control device 16 actually stops driving of the X-ray source 15 until the irradiation of X rays actually stops is also added to the predetermined time TL, and, for example, the timing when the stop timing notification STN is transferred, that is, the predetermined time TL varies depending on, for example, an X-ray source type, or radiographing conditions such as a tube voltage and a tube current.

Figure 30:
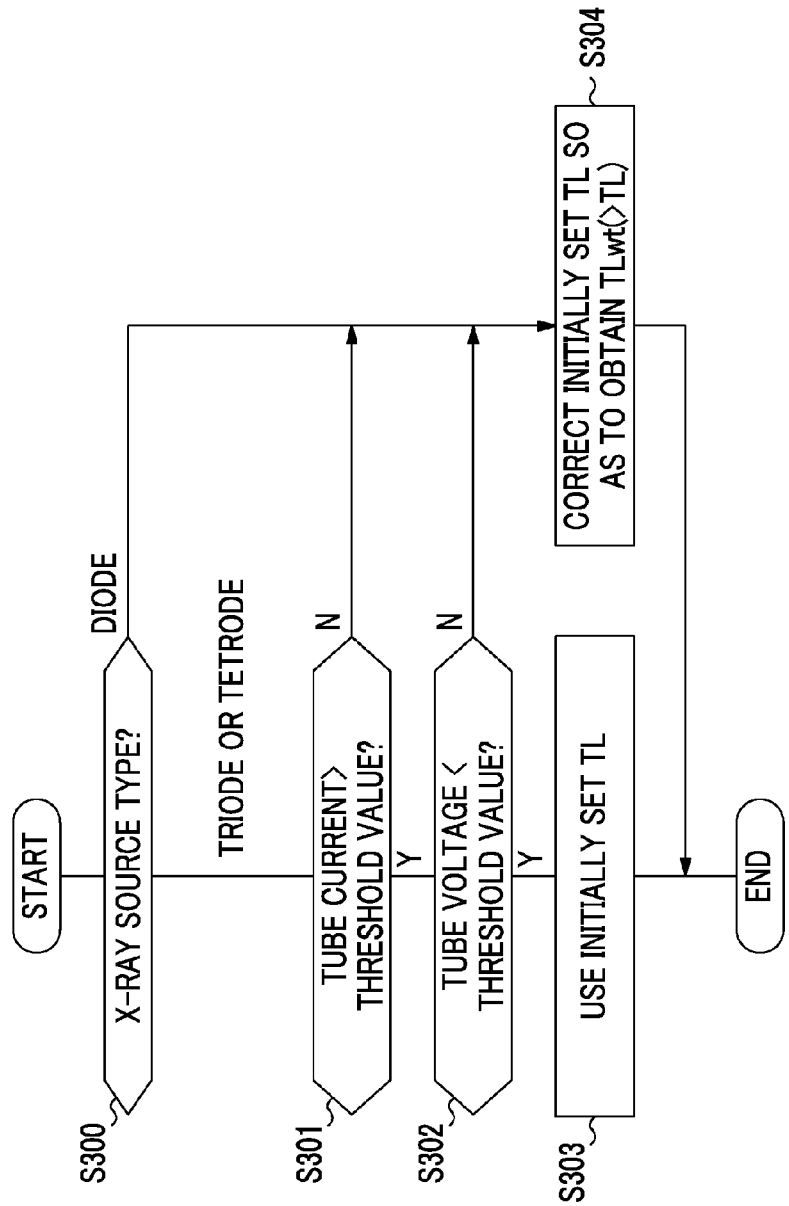
FIG. 30 is a flowchart illustrating procedures of changing a sending timing of a stop timing notification according to an X-ray source and a radiographing condition in the seventh embodiment.

For example, as illustrated in FIG. 30, whether or not the X-ray source 15 is a triode or a tetrode, or a diode is determined (S300), whether or not a tube current is larger than a preset threshold value is determined (S301), and whether or not a tube voltage is smaller than a preset threshold value is determined (S302). In addition, in a case where the X-ray source 15 is a triode or a tetrode, in a case where the tube current is larger than the preset threshold value, or in a case where the tube voltage is smaller than the preset threshold value, the wave tail of the dose of X rays is shortened, and thus overexposure does not occur. Therefore, an initially set predetermined time TL is used (S303). In addition, in a case where the X-ray source 15 is a diode, in a case where the tube current is smaller than the preset threshold value, or in a case where the tube voltage is larger than the preset threshold value, the wave tail of the dose of X rays is lengthened, and thus overexposure occurs. Therefore, the time T is corrected so as to be longer than an initially set value, and thereby a dose of X-ray is prevented from being excessive (S304). Thereby, accuracy of AEC can be improved according to a type of X-ray source or a radiographing condition. In the present embodiment as well, the remaining time RT may be used instead of the scheduled stop time te.

Eighth Embodiment

Figure 31:
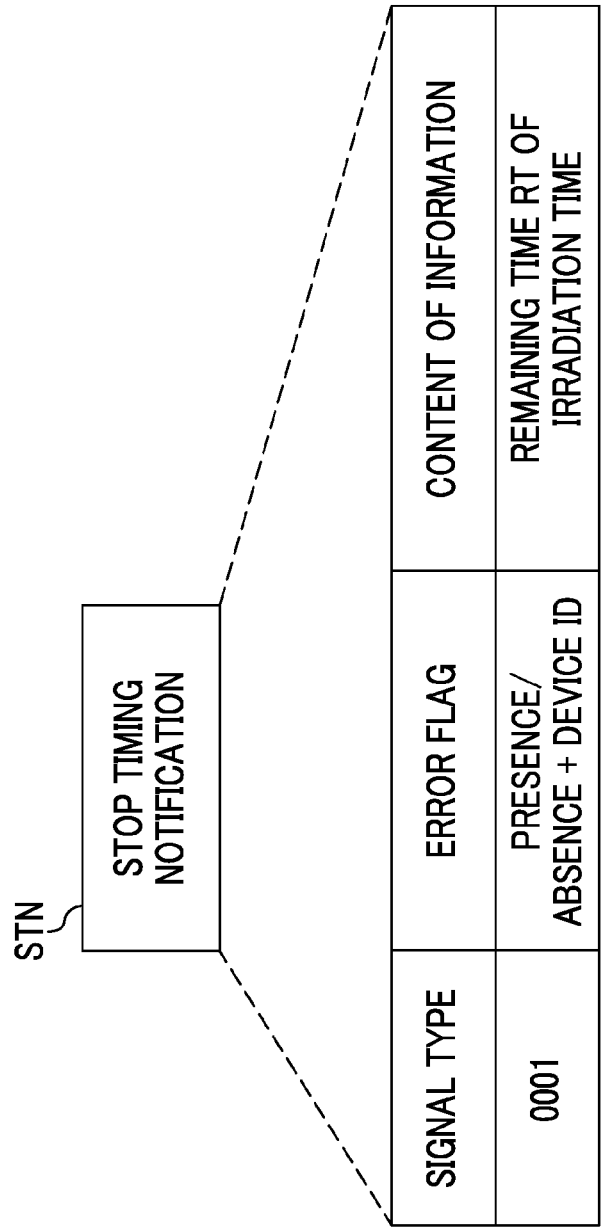
FIG. 31 is a diagram illustrating a data format of a stop timing notification according to an eighth embodiment.
Figure 32:
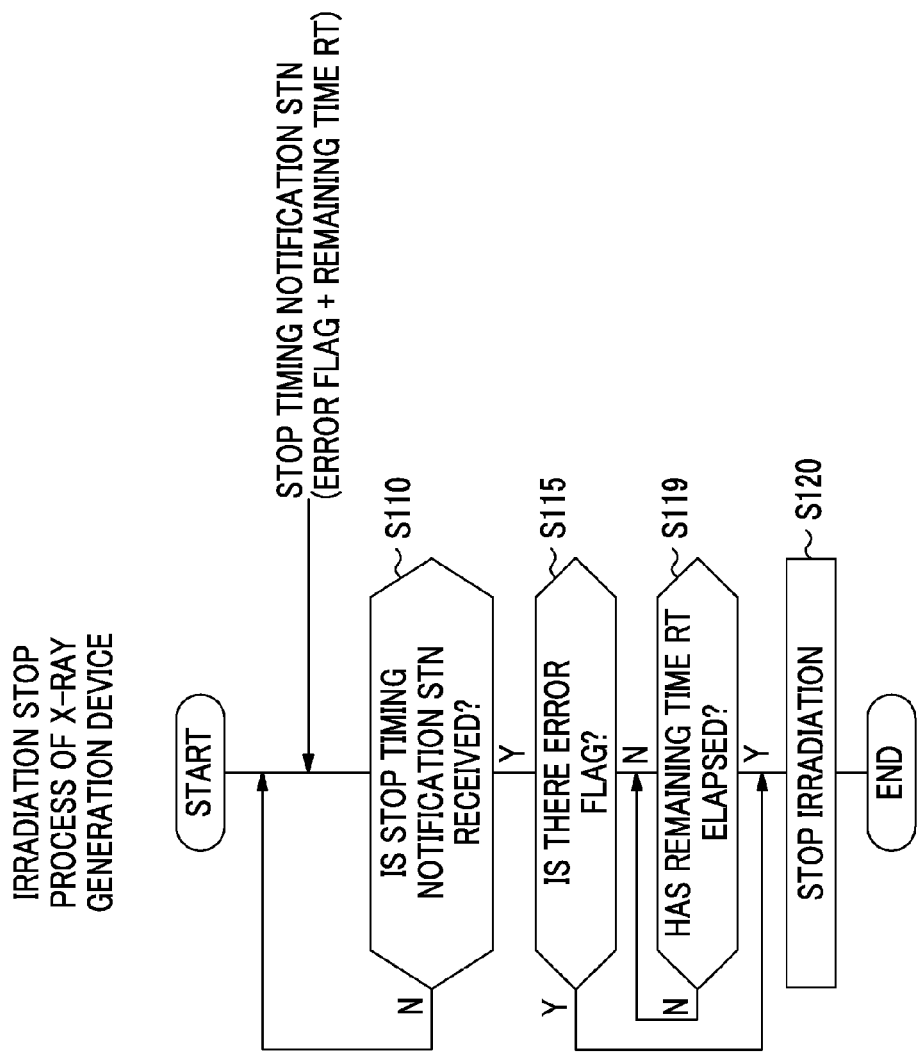
FIG. 32 is a timing chart illustrating procedures of an AEC process according to the eighth embodiment.

As illustrated in FIGS. 31 and 32, the eighth embodiment corresponds to an example in which, as information set in the stop timing notification STN, in addition to a signal type, a remaining time RT or a scheduled stop time te regulating a stop timing, information of presence/absence of an error flag indicating that error occurs in a device and a device ID for identifying the device are set. As the device, for example, there is a relay device such as a switching hub or a router forming a communication path in addition to the electronic cassette 12 and the console 13. An error flag of software may be set in addition to hardware. In a case of software, a software ID is set instead of the device ID.

As illustrated in FIG. 32, the X-ray source control device 16 determines whether or not an error flag is present when the stop timing notification STN is received (S115). In addition, in a case where there is the error flag, emergency stop is unconditionally performed. Thereby, since irradiation immediately stops in a case where error occurs in hardware or software, a danger of continuous irradiation in a state where error occurs can be prevented.

Although, in the above-described embodiment, a description has been made of an example in which the stop timing notification STN is transferred via the console 13 when the stop timing notification STN is transferred from the electronic cassette 12 to the X-ray source control device 16, the electronic cassette 12 and the X-ray source control device 16 may be connected so as to communicate with each other without using the console 13 as illustrated in FIGS. 33 to 37.

Figure 33:
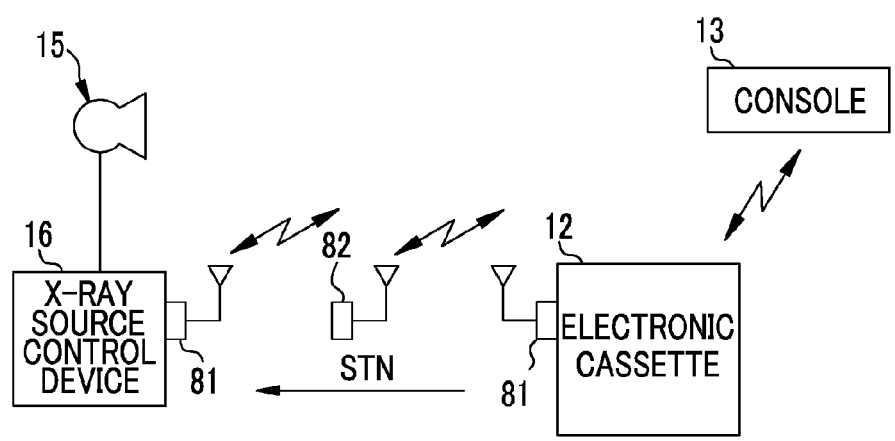
FIG. 33 is a schematic diagram of the X-ray radiographing system in which the electronic cassette and the X-ray source control device are connected to each other in a wireless manner.
Figure 34:
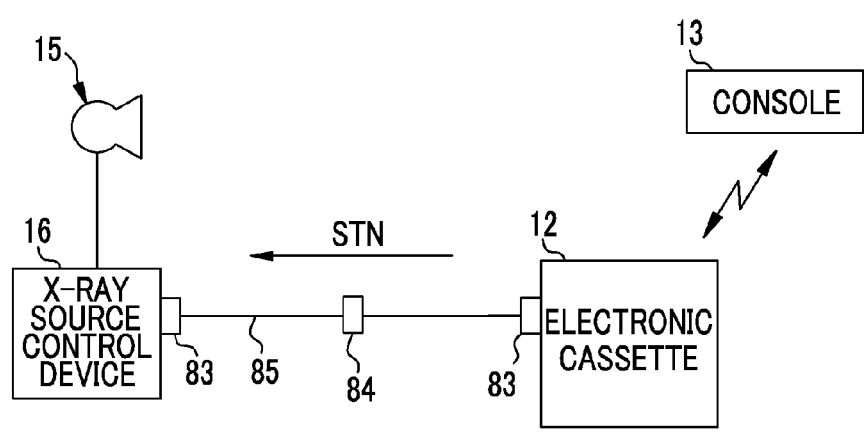
FIG. 34 is a schematic diagram of the X-ray radiographing system in which the electronic cassette and the X-ray source control device are connected to each other in a wired manner.

For example, FIG. 33 illustrates an example in which the electronic cassette 12 and the X-ray source control device 16 are respectively provided with wireless communication units 81 with antennae, respectively, and are connected in a wireless manner. The wireless communication units 81 are connected to each other via a relay device such as a wireless access point 82. In FIG. 34, the electronic cassette 12 and the X-ray source control device 16 are respectively provided with wired communication units 83, and the wired communication units 83 are connected to each other via a cable 85 in a wired manner. A relay device 84 such as a switching hub or a router is interposed on the communication path between the wired communication units 83. According to this example, the console 13 is not interposed, and a time lag of communication can be reduced accordingly.

Figure 35:
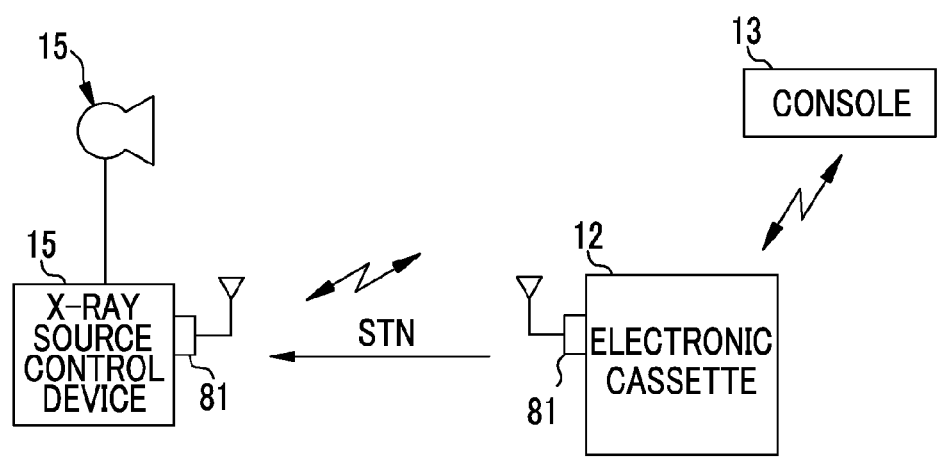
FIG. 35 is a schematic diagram of the X-ray radiographing system in which the electronic cassette and the X-ray source control device are directly connected to each other in a wireless manner.
Figure 36:
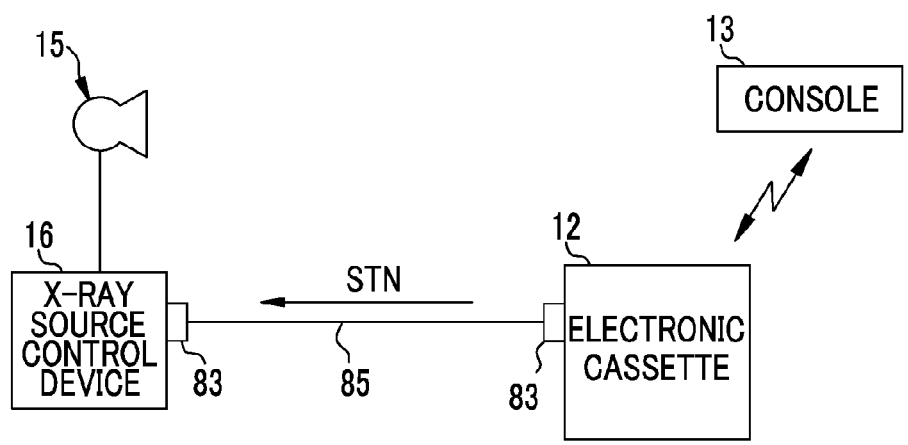
FIG. 36 is a schematic diagram of the X-ray radiographing system in which the electronic cassette and the X-ray source control device are directly connected to each other in a wired manner.

FIGS. 35 and 36 illustrate an example in which the electronic cassette 12 and the X-ray source control device 16 are connected so as to directly communicate with each other without interposing the access point 82 or the relay device 84. FIG. 35 illustrates an example of the wireless manner, and FIG. 36 illustrates an example of the wired manner. According to these examples, since the access point 82 or the relay device 84 is not interposed, a time lag of communication can be further reduced. Since a time lag of communication increases as devices interposed between the electronic cassette 12 and the X-ray source control device 16 increase, direct connection as in this example is useful in the AEC process requiring rapidity.

Figure 37:
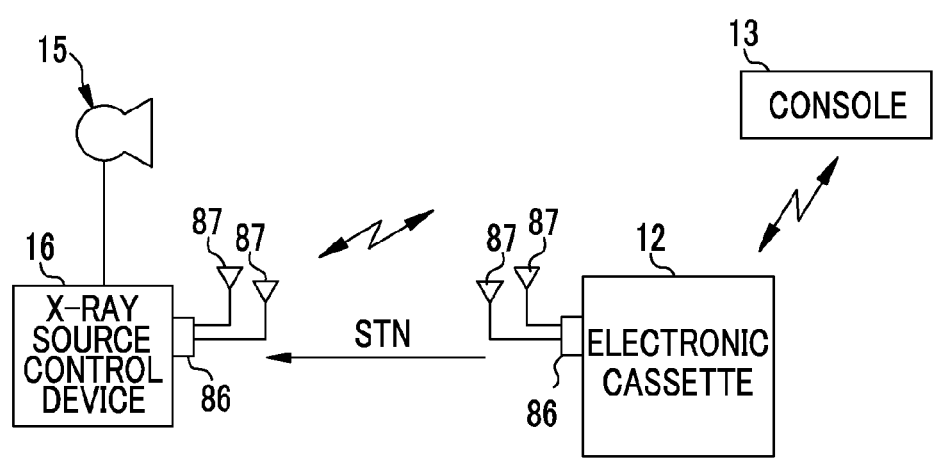
FIG. 37 is a schematic diagram of the X-ray radiographing system in which the electronic cassette and the X-ray source control device are connected to each other using a plurality of wireless channels.

FIG. 37 illustrates a modified example of the example illustrated in FIG. 35, and is an example in which the electronic cassette 12 and the X-ray source control device 16 are respectively provided with wireless communication units 86 which can communicate using a plurality of wireless channels. Each of the wireless communication units 86 is provided with a plurality of transmission and reception antennae 87, and each antenna 87 searches for different wireless channels. Thereby, even in a case where communication failure occurs in any one wireless channel, the stop timing notification STN can be transferred using other wireless channels, and thus a time lag of communication can be reduced. In addition, in the X-ray source control device 16, when a plurality of stop timing notifications STN are received from the respective channels, the latest stop timing notification STN is determined based on content of the stop timing notifications STN.

Although a method of adjusting the predetermined time TL has been described in relation to a time lag of communication, or a time lag until irradiation actually stops from an irradiation stop command as described in the seventh embodiment, for example, a dose target value may be adjusted instead of the predetermined time TL. Specifically, in a case where a time lag is considered to be large, a dose target value decreases, and in a case where a time lag is considered to be small, the dose target value decreases.

Of the above-described embodiments, in the embodiments in which irradiation of X rays stops based on information included in the stop timing notification STN, the stop timing notification STN including the scheduled stop time te or the remaining time RT of an irradiation time is sent from the electronic cassette 12 to the X-ray source control device 16, and the X-ray source control device 16 stops irradiation of X rays based on the scheduled stop time te or the remaining time RT. However, information included in the stop timing notification STN is not limited to the scheduled stop time te or the remaining time RT, and may be other pieces of information as long as the information can be converted into a remaining irradiation time of X rays by the X-ray source control device 16.

As other pieces of information, there is, for example, dose information indicating a remaining irradiation dose of X rays. In a case where the dose information is transferred as content of the stop timing notification STN, information indicating a remaining irradiation dose of X rays can be converted into a remaining irradiation time of X rays based on a tube current of X rays of which irradiation is in progress in the X-ray source control device 16, and thus the irradiation of X rays can stop based on the converted remaining irradiation time. For example, if a remaining irradiation dose of X rays included in the stop timing notification STN is 0 mR (milliroentgens), it is converted into a remaining time of 0 seconds. In this case, the X-ray source control device 16 immediately stops the irradiation of X rays.

In the above-described embodiment, an example in which the electronic cassette 12 self-detects start of irradiation and finish of irradiation has been described, the self-detection may not be performed. In this case, synchronous communication is performed between the X-ray source control device 16 and the electronic cassette 12. For example, when a warm-up start signal from the irradiation switch 17 is received, the X-ray source control device 16 transmits an irradiation start request signal for inquiring whether or not irradiation starts, to the X-ray radiographing device 11 having the electronic cassette 12. In a case of being ready to receive the irradiation, the X-ray radiographing device 11 transmits an irradiation permission signal to the control unit 20 as a response to the irradiation start request.

When the irradiation permission signal is received from the X-ray radiographing device 11 and an irradiation start signal is received from the irradiation switch 17, the control unit 20 issues an irradiation start command to the high voltage generator 19. When the irradiation start command is received, the high voltage generator 19 applies a high voltage to the X-ray source 15 so as to start supplying power. The X-ray source 15 starts irradiation of X rays when power starts to be supplied.

In a case where irradiation by the X-ray source 15 stops, the control unit 20 transmits an irradiation finish signal indicating the irradiation finishes to the X-ray radiographing device 11.

In addition, although, in this example, an arrival dose of X rays is measured by the short-circuited pixel 57 provided in the imaging region 41, the short-circuited pixel 57 has almost the same structure as the typical pixel 40, and has almost the same sensitivity to X rays as the pixel 40. Therefore, there is a merit in that an arrival dose of X rays can be accurately measured. For this reason, prediction accuracy of a stop timing is also high. In addition, the structures thereof are almost the same as each other, and thus manufacturing thereof is easy, and an increase in manufacturing costs is small.

Of course, a dose detection unit is not limited to the short-circuited pixel and may use other aspects. For example, a dedicated pixel for detecting X rays is provided separately from the typical pixels 40 and may be used as the dose detection unit. In addition, by using, for example, a CMOS sensor which can read charge from a typical pixel in a non-destructive manner, a dose of a desired region in the imaging region can be read during irradiation of X rays. Further, as other methods, there is a method in which a current flowing through a bias line for applying a bias voltage to each pixel of the imaging region is detected so as to detect a dose, or a method in which a dose is detected based on a leakage current which leaks to a signal line when the TFT of the typical pixel is turned off. A dose detection unit with any configuration may be used as long as the dose detection unit can detect a dose during irradiation of X rays.

Although, in each of the above-described embodiments, an example in which the electronic cassette 12 and the console 13 are separate devices has been described, the console 13 is not necessarily an independent device, and the X-ray radiographing device 11 may be configured as a single device of the electronic cassette 12 by mounting the functions of the console 13 in the electronic cassette 12. Alternatively, a dedicated radiographing control device having a function regarding control of the electronic cassette 12 may be connected between the electronic cassette 12 and the console 13, and the console 13 may perform only simple works such as an input of radiographing conditions and display of an X-ray image. In addition, the console 13 and the X-ray source control device 16 may be integrally formed. Further, the present invention is not limited to the electronic cassette which is a portable X-ray image detection device and may be applied to an X-ray image detection device type which is fixed to a radiography platform.

In addition, the present invention is not limited to the above-described device configuration and may be applied to other configurations. For example, a dedicated device which receives the stop timing notification STN is provided between the electronic cassette 12 and the X-ray source control device 16, and, in this device, other processes are not performed, and the most part of a CPU may be used for a finish process. In the present invention, in relation to the device configuration of the X-ray image radiographing system, what is not problematic but is important is to prevent a delay of irradiation stop caused by a time lag of communication in a case where a stop timing notification process of AEC is performed over the devices between the electronic cassette 12 and the X-ray source control device 16 which are different devices, and in a case where the electronic cassette 12 side detects an actually irradiated dose and determines whether or not the dose is sufficient relative to a target dose, and the X-ray source control device 16 side which is another device performs actual irradiation stop control via any communication path. Finally, a time lag of communication occurs since a device on a side which detects that irradiation of X rays is sufficient and determines a stop timing and a device which performs actual stop control are separate device, and presence of any device therebetween is not problematic. In this case, the stop timing notification STN is transferred in advance and thereby a delay of irradiation stop timing can be prevented.

In addition, as disclosed in JP2008-086358A, one X-ray radiographing may be performed by a set of pre-irradiation and main irradiation. In this case, transition to an accumulation operation in the main irradiation may be performed in a state where signal charges accumulated in pixels through an accumulation operation in the pre-irradiation are maintained even after the pre-irradiation finishes. In this way, the signal charges obtained through the pre-irradiation can be reflected on an X-ray image without being wasted. In the meaning that exposure which does not contribute to an X-ray image is reduced, an unnecessary exposure of a subject can be reduced.

The present invention is not limited to X rays and may be applied to radiographing systems using other radiation such as y rays. In addition, the present invention is not limited to the above-described respective embodiments and may employ various configurations without departing from the spirit of the present invention.

What is claimed is:

1. A radiographic device which is connected to a radiation generation device irradiating a subject with radiation in order to allow communication therebetween and receives the radiation transferred through the subject so as to radiograph a radiological image of the subject, comprising:
   an image detection unit that has an imaging region where a plurality of pixels accumulating signal charges corresponding to a dose of the radiation are arranged and detects the radiological image;
   a dose detection unit that detects an arrival dose of the radiation arriving at the imaging region;

a stop timing prediction unit that predicts a stop timing for stopping irradiation of the radiation in the radiation generation device based on the arrival dose detected by the dose detection unit and a preset dose target value in order to prevent excess radiation exposure to the subject; and a communication unit that sends a stop timing notification for notifying the stop timing to the radiation generation device before the stop timing arrives, wherein the communication unit sends the stop timing notification a predetermined time before the stop timing, the predetermined time being set in consideration of a time lag of communication with the radiation generation device, and wherein a time lag of the communication is an average time lag derived from multiple measurement points according to a communication path with the radiation generation device.

2. The radiographic device according to claim 1, wherein the stop timing notification includes a scheduled stop time when a cumulative dose which is a cumulative value of the arrival dose is predicted to reach the dose target value.

3. The radiographic device according to claim 1, wherein the stop timing notification includes a remaining time from a reference time point to a time point when a cumulative dose is predicted to reach the dose target value.

4. The radiographic device according to claim 3, wherein the stop timing notification includes a sending time when the communication unit sends the stop timing notification, or an arrival time in the radiation generation device, set in consideration of a time lag of the communication, in addition to the remaining time.

5. The radiographic device according to claim 1, wherein the communication unit sends a plurality of stop timing notifications until the stop timing arrives.

6. The radiographic device according to claim 5, wherein the dose detection unit continuously detects a dose until a cumulative dose which is a cumulative value of the arrival dose reaches the dose target value.

7. The radiographic device according to claim 6, wherein the communication unit sends the plurality of stop timing notifications until the cumulative dose reaches the dose target value.

8. The radiographic device according to claim 6, wherein the stop timing prediction unit performs prediction again when the stop timing notification is sent.

9. The radiographic device according to claim 1, further comprising:
a clock circuit that clocks the current time; and
a synchronization unit that synchronizes the clock circuit with a clock circuit of the radiation generation device.

10. The radiographic device according to claim 1, wherein the communication unit corrects the predetermined time set in consideration of a time lag of the communication based on the kind of the radiation generation device and a radiographing condition for driving the radiation generation device.

11. The radiographic device according to claim 1, wherein the communication unit and the radiation generation device are directly connected to each other without interposing a relay device in a communication path therebetween.

12. The radiographic device according to claim 1, wherein a communication path between the communication unit and the radiation generation device is entirely or partially wireless.

13. The radiographic device according to claim 12, wherein the communication unit is a wireless communication unit.

14. The radiographic device according to claim 13, wherein the wireless communication unit sends the stop timing notification using a plurality of wireless channels.

15. The radiographic device according to claim 1, wherein the stop timing prediction unit corrects the predetermined time set in consideration of a time lag of the communication based on a time from when the communication unit sends a signal to the radiation generation device until the communication unit receives a response to the signal.

16. The radiographic device according to claim 1, wherein the stop timing notification includes an error flag which is given by a communication device which presents in a communication path between the communication unit and the radiation generation device.

17. The radiographic device according to claim 1, further comprising:
a gain setting unit that sets a gain when the radiological image is read from the image detection unit based on the arrival dose detected by the dose detection unit.

18. The radiographic device according to claim 1, wherein the dose detection unit is provided in the imaging region of the image detection unit.

19. A radiographic system comprising:
a radiation generation device that irradiates a subject with radiation; and
a radiographic device that is connected to the radiation generation device in order to allow communication therebetween and receives the radiation transferred through the subject so as to radiograph a radiological image of the subject,
wherein the radiographic device includes
an image detection unit that includes an imaging region where a plurality of pixels accumulating signal charges corresponding to a dose of the radiation are arranged and detects the radiological image;
a dose detection unit that detects an arrival dose of the radiation arriving at the imaging region;
a stop timing prediction unit that predicts a stop timing for stopping irradiation of the radiation in the radiation generation device based on the arrival dose detected by the dose detection unit and a preset dose target value in order to prevent excess radiation exposure to the subject; and
a communication unit that sends a stop timing notification for notifying the radiation generation device of the stop timing to the radiation generation device before the stop timing arrives,
wherein the communication unit sends the stop timing notification a predetermined time before the stop timing, the predetermined time being set in consideration of a time lag of communication with the radiation generation device,
wherein a time lag of the communication is an average time lag derived from multiple measurement points according to a communication path with the radiation generation device, and
wherein the radiation generation device includes
a radiation source that applies the radiation; and
a radiation source control unit that controls the radiation source,
wherein the radiation source control unit includes
a communication unit that receives the stop timing notification; and
a control unit that stops irradiation by the radiation source based on the stop timing notification.

20. The radiographic system according to claim 19, wherein the stop timing notification includes a scheduled stop time when a cumulative dose which is a cumulative value of the arrival dose is predicted to reach the dose target value, and wherein the control unit stops the irradiation by the radiation source based on arrival of the scheduled stop time.

21. The radiographic system according to claim 19, wherein the stop timing notification includes a remaining time from a reference time point to a time point when the cumulative dose is predicted to reach the dose target value, and wherein the control unit stops the irradiation by the radiation source based on the remaining time having elapsed.

22. The radiographic system according to claim 20, wherein the communication unit sends the plurality of stop timing notifications until the stop timing arrives.

23. The radiographic system according to claim 22, wherein the control unit stops the irradiation by the radiation source based on the latest stop timing notification of the plurality of stop timing notifications which have been received.

24. A control method for a radiographic device which is connected to a radiation generation device irradiating a subject with radiation in order to allow communication therebetween and includes an image detection unit provided with an imaging region where a plurality of pixels accumulating signal charges corresponding to a dose of the radiation are arranged and receiving the radiation transferred through the subject so as to detect a radiological image of the subject, comprising:

a dose detection step of detecting an arrival dose of the radiation arriving at the imaging region;

a stop timing prediction step of predicting a stop timing for stopping irradiation of the radiation in the radiation generation device based on the detected arrival dose and a preset dose target value in order to prevent excess radiation exposure to the subject; and a communication step of sending a stop timing notification for notifying the radiation generation device of the stop timing to the radiation generation device before the stop timing arrives wherein the communication step sends the stop timing notification a predetermined time before the stop timing, the predetermined time being set in consideration of a time lag of communication with the radiation generation device, and wherein a time lag of the communication is an average time lag derived from multiple measurement points according to a communication path with the radiation generation device.

25. A non-transitory computer readable recording medium recording thereon a control program for a radiographic device which is connected to a radiation generation device irradiating a subject with radiation in order to allow communication therebetween and includes an image detection unit provided with an imaging region where a plurality of pixels accumulating signal charges corresponding to a dose of the radiation are arranged and receiving the radiation transferred through the subject so as to detect a radiological image of the subject, the control program causing a computer to function as:

a dose detection unit that detects an arrival dose of the radiation arriving at the imaging region;

a stop timing prediction unit that predicts a stop timing for stopping irradiation of the radiation in the radiation generation device based on the arrival dose detected by the dose detection unit and a preset dose target value in order to prevent excess radiation exposure to the subject; and a communication unit that sends a stop timing notification for notifying the radiation generation device of the stop timing to the radiation generation device before the stop timing arrives, wherein the communication unit sends the stop timing notification a predetermined time before the stop timing, the predetermined time being set in consideration of a time lag of communication with the radiation generation device, and wherein a time lag of the communication is an average time lag derived from multiple measurement points according to a communication path with the radiation generation device.

* * * * *